(12) United States Patent
Ramshak

(10) Patent No.: US 7,641,641 B2
(45) Date of Patent: Jan. 5, 2010

(54) ABSORBENT ARTICLE PRODUCT LINE

(75) Inventor: Dana L. Ramshak, Greenville, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 556 days.

(21) Appl. No.: 11/110,512

(22) Filed: Apr. 20, 2005

(65) Prior Publication Data
US 2006/0241558 A1 Oct. 26, 2006

(51) Int. Cl.
A61F 13/15 (2006.01)

(52) U.S. Cl. .................. 604/385.01; 604/385.09; 604/385.11; 604/385.24; 604/385.25; 604/385.29; 604/385.3; 604/392; 604/396; 604/385.101

(58) Field of Classification Search ........... 604/385.25, 604/385.3, 392, 396, 385.01, 385.09, 385.101, 604/385.11, 385.24, 385.29
See application file for complete search history.

(56) References Cited

U.S. PATENT DOCUMENTS

| | | | |
|---|---|---|---|
| 4,122,552 A * | 10/1978 | Tedford | 2/402 |
| 4,230,113 A | 10/1980 | Mehta | |
| 4,351,340 A * | 9/1982 | McLeod | 604/387 |
| 4,615,695 A * | 10/1986 | Cooper | 604/385.15 |
| 4,630,320 A * | 12/1986 | Van Gompel | 2/406 |
| 4,675,015 A | 6/1987 | Brown | |
| 4,699,622 A | 10/1987 | Toussant et al. | |
| 4,769,023 A * | 9/1988 | Goebel et al. | 604/385.21 |
| 4,850,988 A * | 7/1989 | Aledo et al. | 604/385.21 |
| 4,944,733 A | 7/1990 | Casale | |
| 5,074,854 A | 12/1991 | Davis | |
| 5,242,057 A | 9/1993 | Cook et al. | |
| 5,304,158 A | 4/1994 | Webb | |
| 5,370,634 A * | 12/1994 | Ando et al. | 604/385.21 |
| 5,545,158 A * | 8/1996 | Jessup | 604/385.3 |
| 5,622,581 A | 4/1997 | Ducker et al. | |
| 5,624,420 A | 4/1997 | Bridges et al. | |
| 5,690,626 A * | 11/1997 | Suzuki et al. | 604/385.25 |
| 5,704,929 A * | 1/1998 | Bien | 604/385.23 |
| 5,836,930 A * | 11/1998 | Lantz et al. | 604/378 |
| 5,839,585 A | 11/1998 | Miller | |
| 5,865,322 A | 2/1999 | Miller | |
| 5,897,542 A | 4/1999 | Lash et al. | |

(Continued)

FOREIGN PATENT DOCUMENTS

FR 2604867 A1 4/1988

OTHER PUBLICATIONS

Huggies Convertibles Diaper-Pants website printout (1 page) admitted prior art.

(Continued)

Primary Examiner—Tatyana Zalukaeva
Assistant Examiner—Ginger T Chapman
(74) Attorney, Agent, or Firm—Armstrong Teasdale LLP

(57) ABSTRACT

A product line of absorbent articles includes a first absorbent article with a first elective component secured to the first absorbent article in a first configuration of the component. The first elective component is selectively configurable to a second configuration different from the first configuration of the component. A second absorbent article of the product line has a second elective component that is selectively configurable from a first configuration of the second elective component to a second configuration different from the first configuration of the second elective component.

9 Claims, 31 Drawing Sheets

U.S. PATENT DOCUMENTS

| | | | |
|---|---|---|---|
| 5,968,028 A | 10/1999 | Roe et al. | |
| 5,989,236 A * | 11/1999 | Roe et al. | 604/385.04 |
| 6,004,306 A | 12/1999 | Robles et al. | |
| 6,027,484 A | 2/2000 | Romare | |
| 6,056,732 A | 5/2000 | Fujioka et al. | |
| 6,093,027 A | 7/2000 | Unger et al. | |
| 6,102,899 A * | 8/2000 | Yimin | 604/385.01 |
| 6,110,157 A | 8/2000 | Schmidt | |
| 6,368,113 B1 | 4/2002 | Unger et al. | |
| 6,454,095 B1 | 9/2002 | Brisebois et al. | |
| 6,497,696 B1 | 12/2002 | Freiburger et al. | |
| 6,508,797 B1 | 1/2003 | Pozinak et al. | |
| 6,568,530 B2 | 5/2003 | Takahashi et al. | |
| 6,575,949 B1 | 6/2003 | Waksmundzki et al. | |
| 6,579,275 B1 | 6/2003 | Pozniak et al. | |
| 6,604,609 B2 | 8/2003 | Bruce et al. | |
| 6,623,466 B1 | 9/2003 | Richardson | |
| 6,648,864 B2 | 11/2003 | Ronn et al. | |
| 6,702,798 B2 | 3/2004 | Christoffel et al. | |
| 6,763,944 B2 | 7/2004 | Ronn et al. | |
| 2003/0114808 A1 | 6/2003 | Underhill et al. | |
| 2003/0135186 A1 * | 7/2003 | Olson et al. | 604/385.01 |
| 2004/0010240 A1 | 1/2004 | Ronn et al. | |
| 2004/0030308 A1 * | 2/2004 | Ronn et al. | 604/358 |
| 2004/0186451 A1 * | 9/2004 | Bishop et al. | 604/385.11 |
| 2004/0225271 A1 | 11/2004 | Datta et al. | |
| 2005/0192553 A1 * | 9/2005 | Hasler et al. | 604/385.11 |
| 2005/0222549 A1 * | 10/2005 | Balogh | 604/385.11 |
| 2005/0256493 A1 * | 11/2005 | Datta et al. | 604/385.29 |
| 2006/0047260 A1 | 3/2006 | Ashton et al. | 604/396 |
| 2006/0212013 A1 * | 9/2006 | Cohen et al. | 604/385.09 |
| 2006/0241558 A1 | 10/2006 | Ramshak | |

OTHER PUBLICATIONS

Pull-Ups Training Pants website printout (2 pages) admitted prior art.
International Search Report for PCT/US2006/003682 dated Nov. 3, 2006, 8 pages.
Non-final office action regarding U.S. Appl. No. 11/440,674, dated Jan. 8, 2009.

* cited by examiner

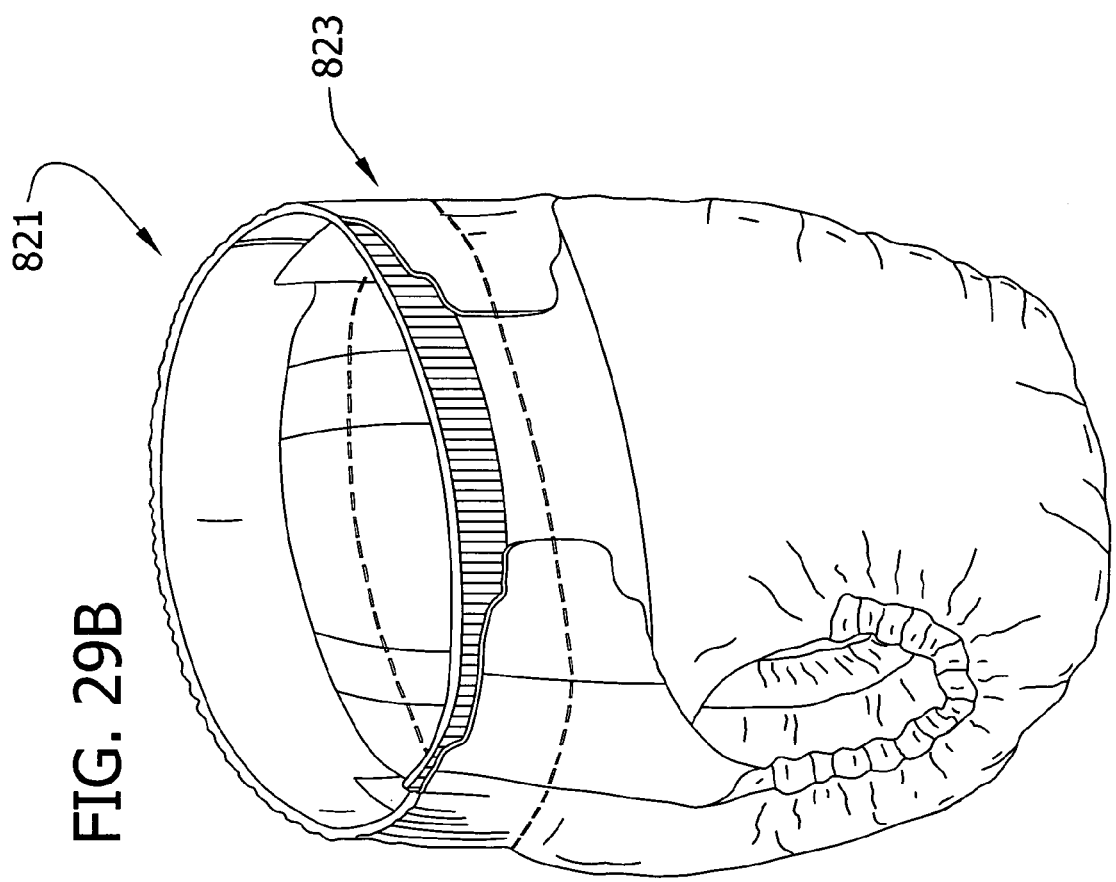
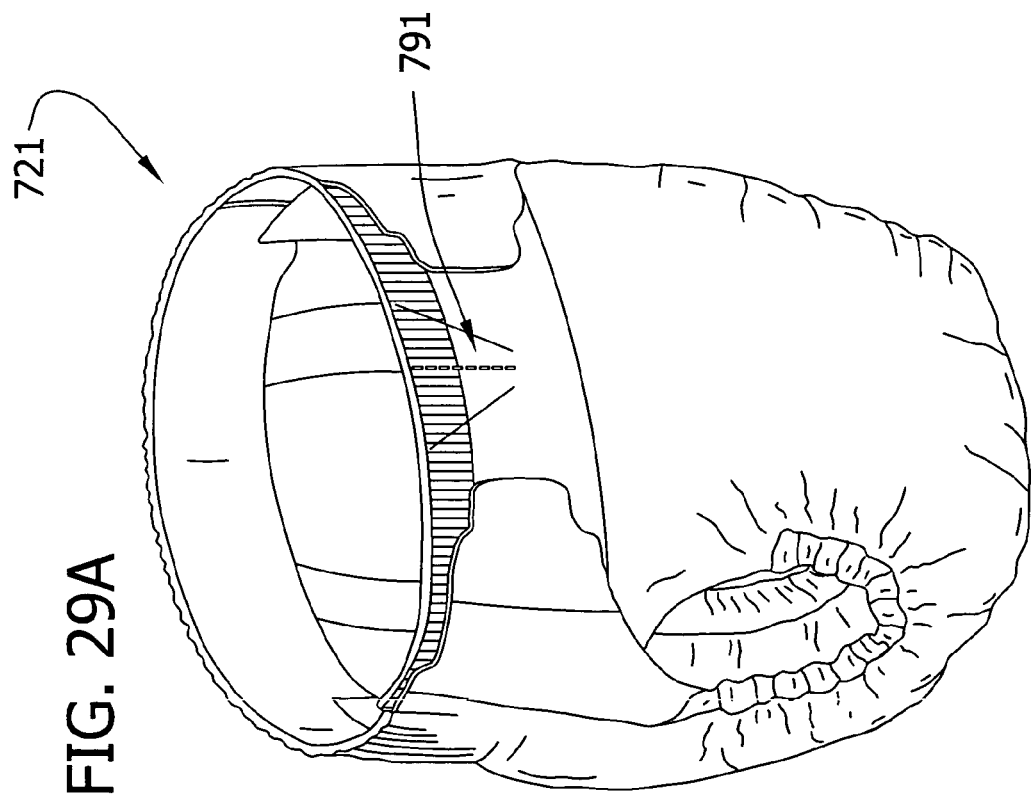

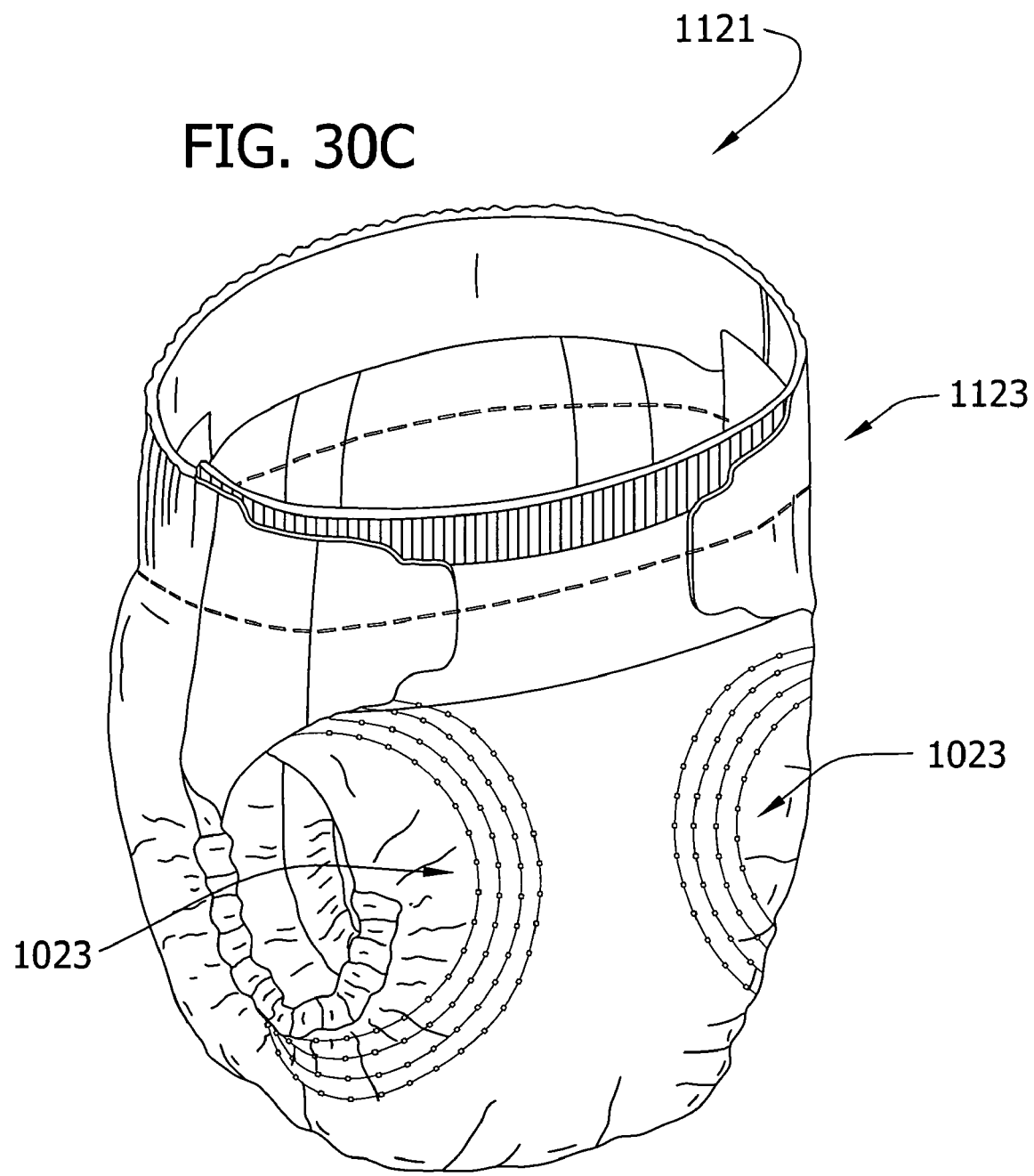

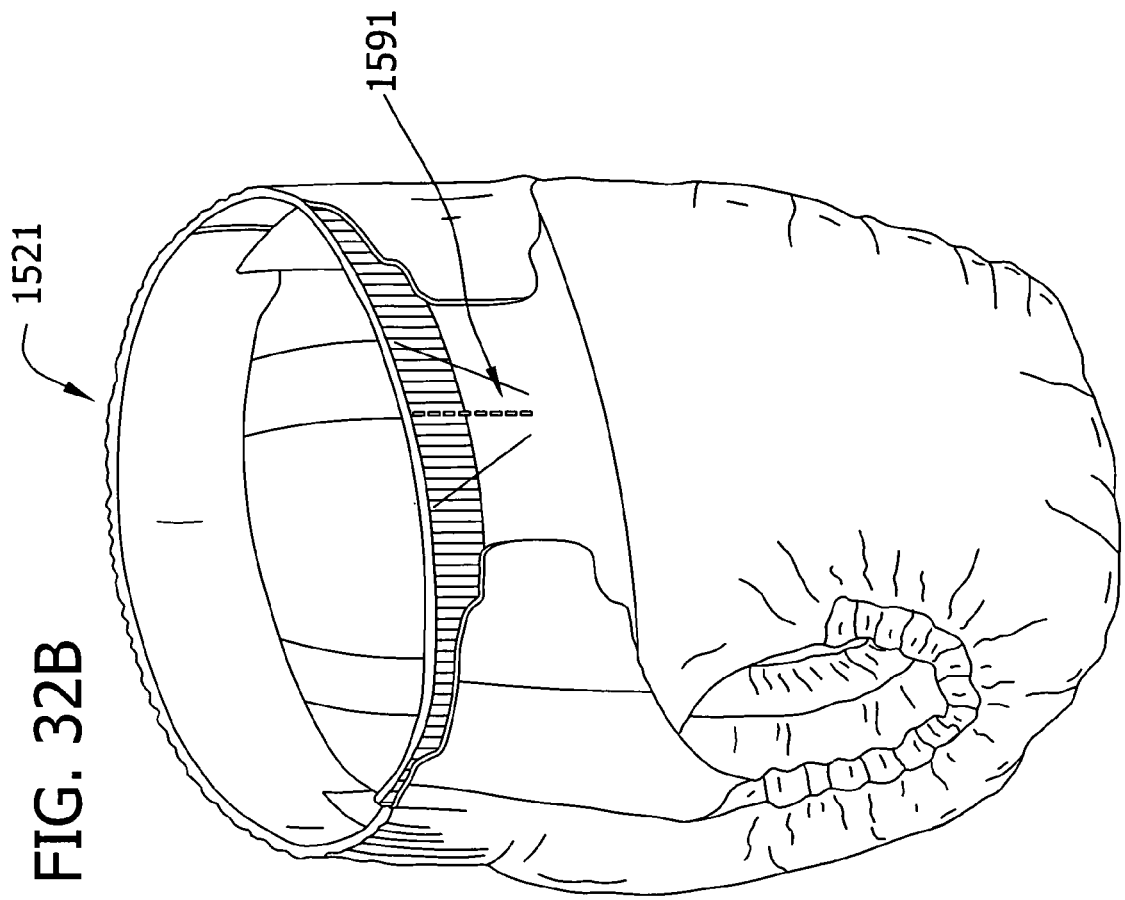
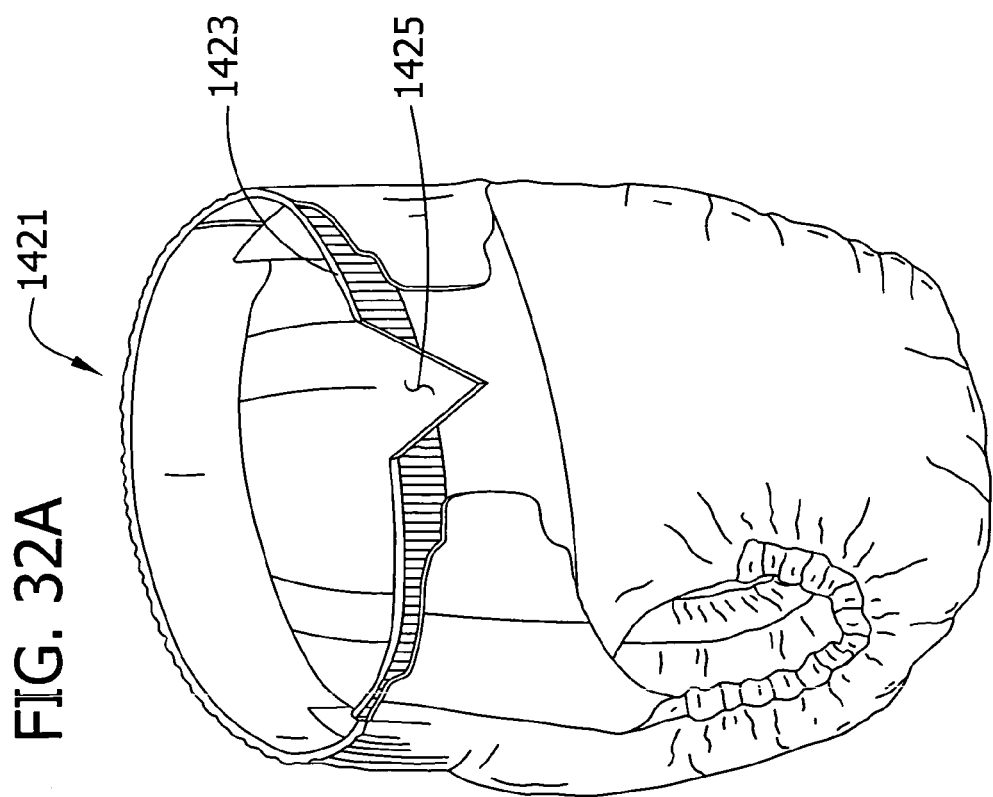

ABSORBENT ARTICLE PRODUCT LINE

BACKGROUND OF THE INVENTION

Disposable absorbent articles, such as infant diapers, child training pants, adult incontinence briefs, undergarments and refastenable underwear, and feminine hygiene products are well known for their use in absorbing and retaining liquid and/or solid discharges from the human body. Often, a line of similar type absorbent articles are made commercially available to fit wearers of different size (e.g., waist size, weight, etc.), age, activity or the like. For example, Kimberly-Clark Corporation of Neenah, Wis. offers a product line of diapers under the trademark HUGGIES®, which come in various sizes geared for different size ranges (e.g., weight ranges) of intended wearers.

However, the size of the user, while a suitable guidepost for the majority of users, is not a direct indication of all user needs. Rather, absorbent articles are more typically designed to fit the average sized wearer within a particular size range. As a result, fit features of the articles, such as waist openings, leg openings, length of the article (i.e., pitch) and rise (e.g., where the waist line seats on the wearer's body) are all configured for the average user within a size range. But there are additional users within a particular size range who do not have the average body configuration, such as those users at the lower and upper ends of a given size. For example, a diaper sized for users between 16 pounds and 28 pounds would likely fit an infant weighting 22 pounds better than one weighing 16 or 28 pounds. In another example, caregivers of newborn babies that are too big for newborn diapers are unable to find larger diapers designed to accommodate the infant's umbilical cord. Good fit for absorbent articles is important for user comfort and good product performance since the fit of the article plays a critical role in management of body waste.

Moreover, wearer's often desire a particular look (e.g., appearance) for absorbent articles. For example, some caregivers and/or adult incontinent brief wearers may prefer a more boxer or brief style appearance while others prefer a trimmer, more bikini type appearance. As another example, some like the rise of the absorbent article to seat relatively high on a wearer's waist line while others prefer a lower rise appearance. However, commercially offering various absorbent articles designed to accommodate each persons desired appearance and/or fit preference can be costly and inefficient.

There is a need, therefore, for a product line of absorbent articles in the which two or more articles in the product line each have an elective component that allow a caregiver or wearer to selectively configure the article to a desired appearance or fit configuration.

SUMMARY OF THE INVENTION

In general, one aspect of the present invention is direct to a product line of absorbent articles comprises a first absorbent article adapted to fit wearers sized within a first size range, and a second absorbent article adapted to fit wearers sized within a second size range at least in part different from the first size range. The first and second absorbent articles comprise an outer cover, a liquid permeable bodyside liner in opposed relationship with the outer cover, an absorbent body disposed between the liner and the outer cover for absorbing liquid that passes through the liner. A first elective component is secured to the first absorbent article in a first configuration of the component and selectively configurable to a second configuration different from the first configuration of the component. A second elective component, which is different from the first elective component, is secured to the second absorbent article in a first configuration of the second elective component. The second elective component is selectively configurable to a second configuration different from the first configuration of the second elective component.

In another aspect of the present invention, a product line of absorbent articles comprises a first absorbent article adapted to fit wearers sized within a first size range, and a second absorbent article adapted to fit wearers sized within a second size range at least in part different from the first size range. The first and second absorbent article comprise an outer cover, a liquid permeable bodyside liner in opposed relationship with the outer cover, an absorbent body disposed between the liner and the outer cover for absorbing liquid that passes through the liner. A first elective component is attached to the article in a first configuration of the first elective component and selectively configurable to a second configuration different from the first configuration of the first elective component. The first absorbent article is sized for use of the first elective component in its first configuration by a minority of wearers sized within the first size range and for use of the first elective component in its second configuration by a majority of wearers sized within the first size range. A second elective component is substantially the same as the first elective component and attached to the second absorbent article in a first configuration of the second elective component. The second elective component is selectively configurable to a second configuration different from the first configuration of the second elective component. The second absorbent article is sized for use of the second elective component in its first configuration by a majority of wearers sized within the second size range and for use of the second elective component in its second configuration by a minority of wearers sized within the second size range.

In yet another aspect of the present invention, a product line of absorbent article comprises a first absorbent article adapted to fit wearers sized within a first size range, a second absorbent article adapted to fit wearers sized within a second size range at least in part different from the first size range, and a third absorbent article adapted to fit wearers sized within a third size range at least in part different from the first and second size ranges. The first, second, and third absorbent articles comprise an outer cover, a liquid permeable bodyside liner in opposed relationship with the outer cover, an absorbent body disposed between the liner and the outer cover for absorbing liquid that passes through the liner. A first elective component is secured to the first absorbent article in a first configuration of the component and selectively configurable to a second configuration different from the first configuration of the component. A first elective component, which is substantially the same as the first elective component of the first absorbent article, and a second elective component, which is different from the first elective component, is secured to the second absorbent article in a first configuration of the second elective component. The second elective component is selectively configurable to a second configuration different from the first configuration of the second elective component. A first elective component, which is substantially the same as at least one of the first elective component of the second absorbent article and the second elective component of the second absorbent article, and a second elective component, which is different from the first elective component of the third absorbent article, is secured to the third absorbent article in a first configuration of the second elective component. The second elective component is selectively configurable to a second configuration different from the first configuration of the second elective component.

In still yet another aspect of the present invention, a product line of absorbent articles comprises a first absorbent article and a second absorbent article. Each of the absorbent articles comprises an outer cover, a liquid permeable bodyside liner in opposed relationship with the outer cover, an absorbent body disposed between the liner and the outer cover for absorbing liquid that passes through the liner. A first elective component is secured to the first absorbent article in a first configuration of the component and selectively configurable to a second configuration different from the first configuration of the component. The first elective component is associated with at least one body characteristic of the wearer. A second elective component, which is different from the first elective component, is secured to the second absorbent article in a first configuration of the second elective component. The second elective component is selectively configurable to a second configuration different from the first configuration of the second elective component. The second elective component is associated with at least one body characteristic of the wearer different from the at least one body characteristic with which the first elective component is associated.

In yet a further aspect of the present invention, a product line of absorbent articles comprises a first absorbent article and a second absorbent article. Each of the absorbent articles comprises an outer cover, a liquid permeable bodyside liner in opposed relationship with the outer cover, an absorbent body disposed between the liner and the outer cover for absorbing liquid that passes through the liner. The first absorbent article is permanently configured to accommodate at least one body characteristic of the wearer. An elective component is secured to the second absorbent article in a first configuration of the second elective component. The elective component is selectively configurable to a second configuration different from the first configuration of the elective component. In the second configuration of the elective component, the second absorbent article is configured to accommodate the at least one body characteristic of the wearer.

Other objects and features will be in part apparent and in part pointed out hereinafter.

BRIEF DESCRIPTION OF THE DRAWINGS

FIG. 29A is a perspective view of a diaper of a product line of absorbent articles, with the diaper having an elective component in the form of an umbilical cord component;

FIG. 29B is a perspective view of another diaper in the product line, with this other diaper having an elective component in the form of a waist line component;

FIG. 30C is a perspective view of a third diaper of the product line, with the third diaper having a first elective component in the form of a leg opening component and a second elective component in the form of a waist line component;

FIG. 32A is a perspective view of a first diaper of a fourth embodiment of a product line of absorbent articles, with the first diaper having an umbilical cord cut out;

FIG. 32B is a perspective view of a second diaper of the product line with the second diaper having an elective component in the form of an umbilical cord component;

Corresponding reference characters indicate corresponding parts throughout the several views of the drawings.

DETAILED DESCRIPTION

Figure 1:
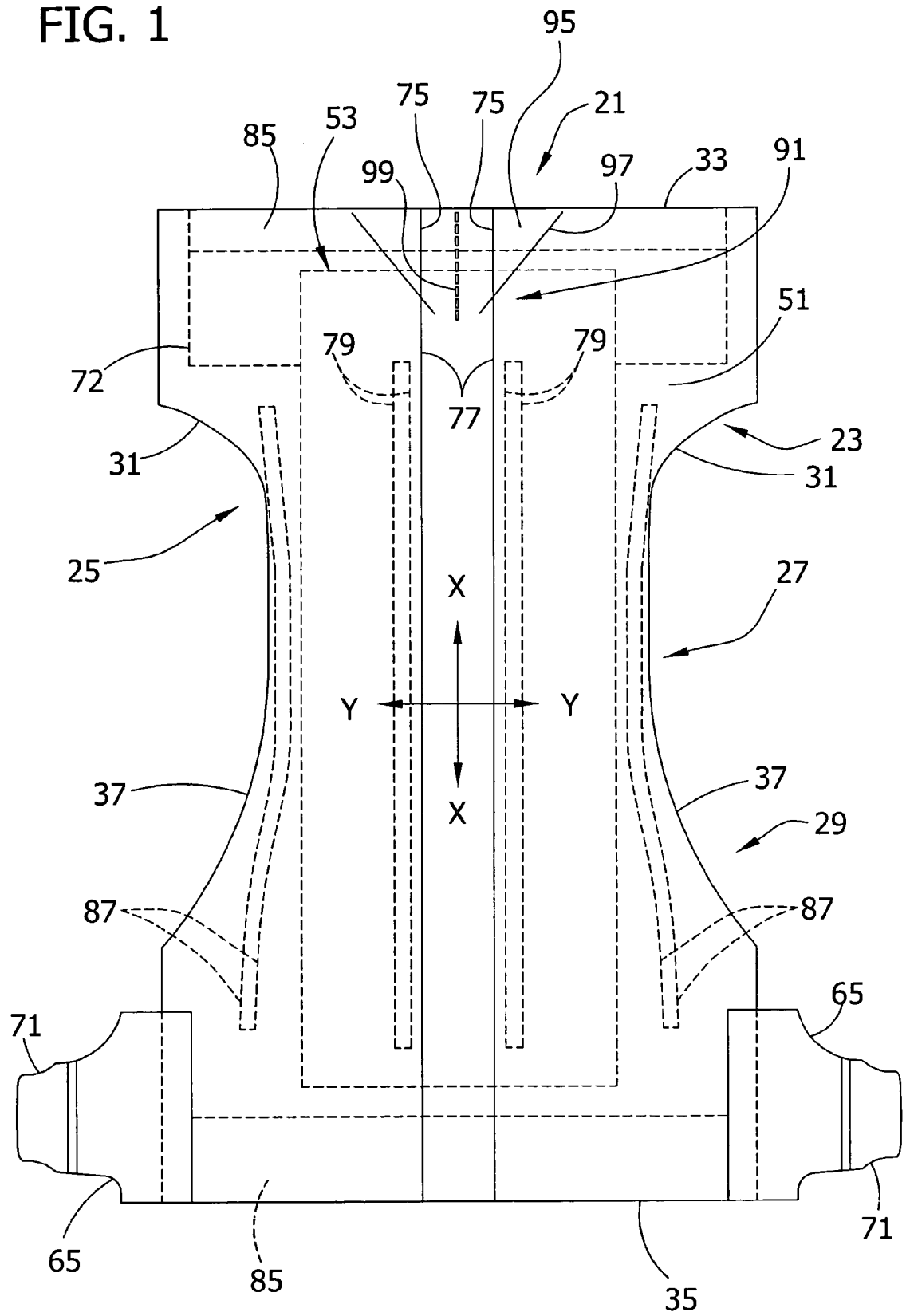
FIG. 1 is a top plan view of a diaper in an unfolded and laid flat condition to show an inner surface of the diaper which faces the wearer when the diaper is worn, the diaper having an elective component in the form of an umbilical component.

The present invention is directed generally to a product line of disposable absorbent articles, with some or all of the articles in the product line having one or more elective components that allow a wearer (or a caregiver) to selectively customize the configuration of the article to change the fit, look, comfort level or use of the article. As used herein, an absorbent article refers to an article which may be placed against or in proximity to the body of the wearer (e.g., contiguous to the body) to absorb and/or retain various waste discharged from the body. Disposable absorbent articles, are intended to be discarded after a limited period of use instead of being laundered or otherwise restored for reuse. It is contemplated, however, that the principles of the present invention have application in garments (including reusable garments) and other absorbent articles. In particularly suitable embodiments of the present invention, the disposable absorbent articles fall within the group of absorbent articles that are intended to be worn about a wearer's waist, such as diapers, children's training pants and adult incontinence briefs, for taking in and retaining urine and feces. It is understood, however, that the product line of the present invention is equally applicable to other absorbent articles such as feminine hygiene products and medical garments.

The term "product line" as used herein refers to a set of at least two articles available from a single source and having a substantially similar function (e.g., taking in and retaining bodily exudates) but otherwise differing in at least one characteristic such as an elective component, style, model, size and the like. For example, it is known to provide a product line of diapers comprised of a set of two or more diapers with each diaper in the set corresponding to a respective different size (e.g., weight) of the intended wearer. An elective component of the absorbent article refers to a component of the article that is initially (e.g., upon manufacturing of the article) in a first configuration and may be selectively reconfigured by the wearer or caregiver to a second configuration different from the first configuration to reconfigure the article.

Referring now to the drawings, FIGS. 1-27, various absorbent articles having an elective component suitable for use in a product line of absorbent articles in accordance with the present invention are illustrated. It is understood that while the various elective components are shown in the drawings and described herein with each elective component incorporated on a particular absorbent article (e.g., a diaper, training pants or adult incontinence brief), the elective components may be provided on other absorbent articles, depending on the desired product line, without departing from the scope of this invention.

Figure 2:
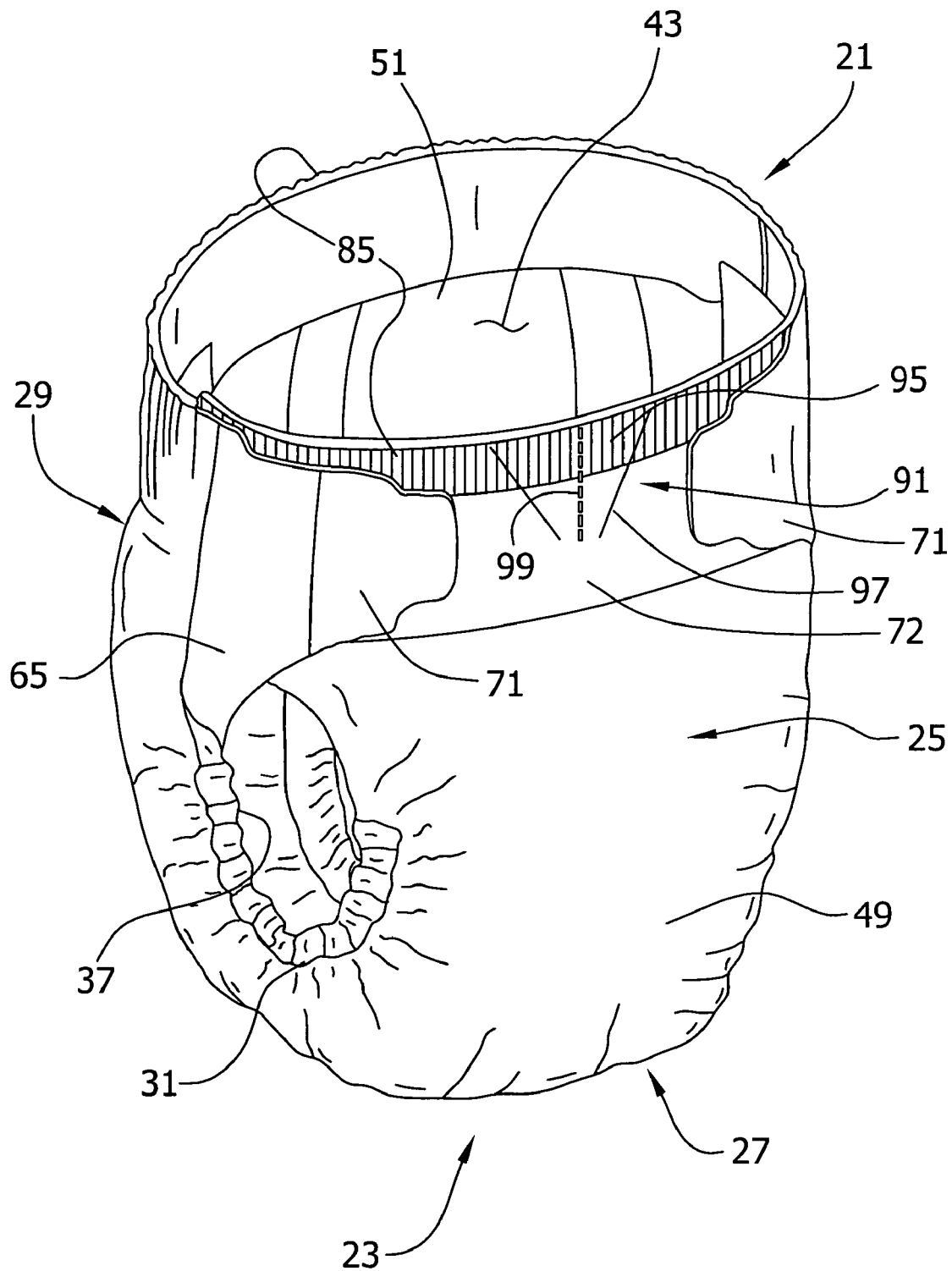
FIG. 2 is a perspective view of the diaper of FIG. 1 in a fastened configuration and in a first configuration of the umbilical cord component.
Figure 3:
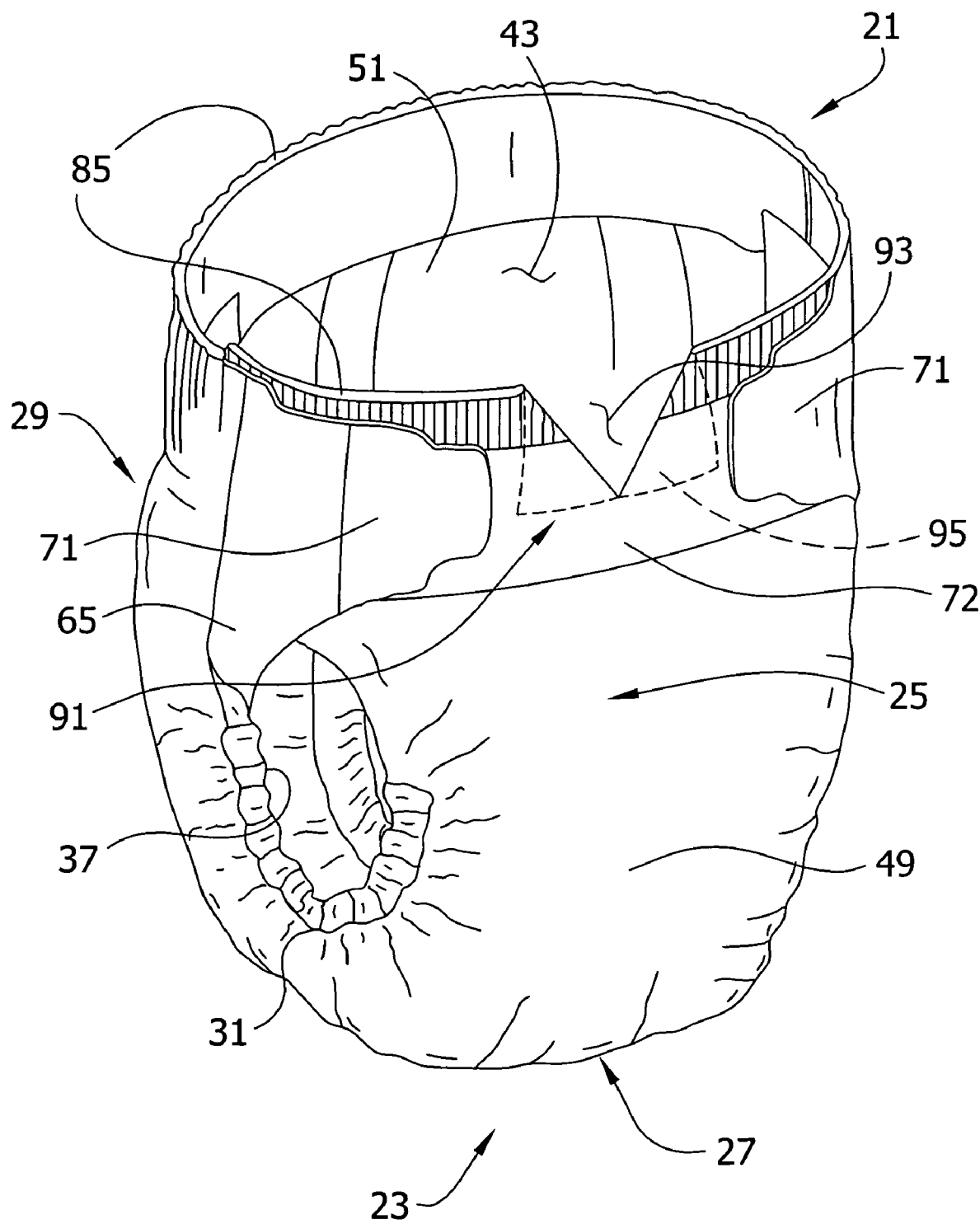
FIG. 3 is a perspective view similar to FIG. 2 with the umbilical cord component in a second configuration for accommodating the wearer's umbilical cord.

With particular reference to FIGS. 1-3, a disposable absorbent article is illustrated in the form of a diaper, indicated generally at 21. The diaper 21 is shown in FIG. 1 in an unfolded and laid-flat condition to illustrate a longitudinal axis X and a lateral axis Y of the diaper. The diaper 21 generally comprises a central absorbent assembly 23 extending longitudinally from a front (e.g., anterior) region 25 of the diaper through a crotch (e.g., central) region 27 to a back (e.g., posterior) region 29 of the diaper. The front region 25 generally includes the portions of the central absorbent assembly 23 which extend over the wearer's lower abdominal region and the back region 29 generally includes the portions of the central absorbent assembly which extend over the wearer's lower back region. The crotch region 27 includes the portion extending longitudinally through the wearer's crotch from the front region 25 to the back region 29 and laterally between the wearer's legs.

The central absorbent assembly 23 is generally I-shaped, and more particularly hourglass shaped, and has contoured, laterally opposite side edges 31 and longitudinally opposite front and rear waist edges or ends, respectively designated 33 and 35. It is understood, however, that the diaper 21 may have other shapes, such as a rectangular shape or a T-shape without departing from the scope of the present invention. The side edges 31 of the diaper 21 extend longitudinally from the front region 25 through the crotch region 27 to the back region 29 for forming transversely spaced leg openings 37 (FIG. 2) of the diaper when worn. As worn on the wearer's body (FIG. 2), the diaper 21 further defines a central waist opening 43 and the leg openings 37.

The central absorbent assembly 23 of the diaper 21 comprises an outer cover, generally indicated at 49 in FIG. 1, a bodyside liner 51 (FIG. 1) positioned in opposed relation with the outer cover, and an absorbent structure, generally indicated at 53 in FIG. 1, of the present invention disposed between the outer cover and the liner. The outer cover 49 of the illustrated embodiment generally defines the length and width of the diaper 21. The absorbent structure 53 has a length and width which are each less than the respective length and width of the outer cover 49 such that the outer cover extends both longitudinally and laterally out beyond the sides and ends of the absorbent structure. The bodyside liner 51 may be generally coextensive with the outer cover 49, or may instead overlie an area which is larger (and would thus generally define the length and/or width of the diaper 21) or smaller than the area of the outer cover 49, as desired. In other words, the bodyside liner 51 is in superposed relationship with the outer cover 49 but may not necessarily be coextensive with the outer cover.

In one embodiment, the outer cover 49 is stretchable and may or may not be somewhat elastic. More suitably, the outer cover 49 is sufficiently extensible such that once stretched under the weight of the insulted absorbent structure, the outer cover will not retract substantially back toward its original position. However, it is contemplated that the outer cover 49 may instead be generally non-extensible and remain within the scope of this invention.

The outer cover 49 may be a multi-layered laminate structure to provide desired levels of extensibility as well as liquid impermeability and vapor permeability. For example, the outer cover 49 of the illustrated embodiment is of two-layer construction, including an outer layer constructed of a vapor permeable material and an inner layer constructed of a liquid impermeable material, with the two layers being secured together by a suitable laminate adhesive. It is understood, however, that the outer cover 49 may instead be constructed of a single layer of liquid impermeable material, such as a thin plastic film, without departing from the scope of this invention. The liquid impermeable inner layer of the outer cover 49 can be either vapor permeable (i.e., "breathable") or vapor impermeable.

The bodyside liner 51 is suitably pliable, soft feeling, and nonirritating to the wearer's skin, and is employed to help isolate the wearer's skin from the absorbent structure 53. The liner 51 is less hydrophilic than the absorbent structure 53 to present a relatively dry surface to the wearer, and is sufficiently porous to be liquid permeable to thereby permit liquid to readily penetrate through its thickness. A suitable bodyside liner 51 may be manufactured from a wide selection of web materials, but is suitably capable of stretching in at least one direction (e.g., longitudinal or lateral). In particular embodiments, the bodyside liner 51 is extensible and capable of extending along with the outer cover 49 for desired fit of the diaper 21 on the wearer.

Fastener tabs 65 are secured to the central absorbent assembly 23 generally at the back region 29 thereof with the tabs extending laterally out from the opposite side edges 31 of the assembly. The fastener tabs 65 may be attached to the outer cover 49, to the bodyside liner 51, between the outer cover and liner, or to other components of the diaper 21. The tabs 65 may also be elastic or otherwise rendered elastomeric. For example, the fastener tabs 65 may be an elastomeric material such as a neck-bonded laminate (NBL) or stretch-bonded laminate (SBL) material.

Methods of making such materials are well known to those skilled in the art and are described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987 in the names of Taylor et al., the disclosures of which are hereby incorporated by reference. Examples of articles that include selectively configured fastener tabs are described in U.S. Pat. No. 5,496,298 issued Mar. 5, 1996 to Kuepper et al.; U.S. Pat. No. 5,540,796 to Fries; and U.S. Pat. No. 5,595,618 to Fries; the disclosures of which are also incorporated herein by reference. Alternatively, the fastener tabs 65 may be formed integrally with a selected diaper component. For example, the tabs may be formed integrally with the inner or outer layer of the outer cover, or with the bodyside liner.

Fastening components, such as hook and loop fasteners, designated 71 and 72 respectively, are employed to secure the diaper 21 on the body of a child or other wearer. Alternatively, other fastening components (not shown), such as buttons, pins, snaps, adhesive tape fasteners, cohesives, mushroom-and-loop fasteners, or the like, may be employed. Desirably, the interconnection of the fastening components 71, 72 is selectively releasable and re-attachable. In the illustrated embodiment, the hook fasteners 71 are secured to and extend laterally out from the respective fastener tabs 65 at the back region 29 of the diaper 21. However, it is understood that the fastener tabs 65 may be formed of a hook material and thus comprise the hook fasteners 71 without departing from the scope of this invention. The loop fastener 72 of the illustrated embodiment is a panel of loop material secured to the outer cover 49 at the front region 25 of the diaper 21 to provide a "fasten anywhere" mechanical fastening system for improved fastening of the hook fasteners 71 with the loop fastener.

The diaper 21 shown in FIG. 1 also comprises a pair of containment flaps 75 configured to provide a barrier to the lateral flow of body exudates. The containment flaps 75 are located generally adjacent laterally opposite side edges 31 of the diaper 21 and, when the diaper is laid flat as shown in FIG. 1 extend inward toward the longitudinal axis X of the diaper. Each containment flap 75 typically has a free, or unattached end 77 free from connection with the bodyside liner 51 and other components of the diaper 21. Elastic strands 79 disposed within the flaps 75 adjacent the unattached ends thereof urge the flaps toward an upright, perpendicular configuration in at least the crotch region 27 of the diaper 21 to form a seal against the wearer's body when the diaper is worn. The containment flaps 75 may extend longitudinally the entire length of the diaper 21 or they may extend only partially along the length of the diaper. When the containment flaps 75 are shorter in length than the diaper 21, the flaps can be selectively positioned anywhere between the side edges 31 of the diaper 21 in the crotch region 27. In a particular aspect of the invention, the containment flaps 75 extend the entire length of the diaper 21 to better contain the body exudates.

Such containment flaps 75 are generally well known to those skilled in the art and therefore will not be further described herein except to the extent necessary to describe the present invention. As an example, suitable constructions and arrangements for containment flaps 75 are described in U.S. Pat. No. 4,704,116 issued Nov. 3, 1987, to K. Enloe, the disclosure of which is hereby incorporated by reference. The diaper 21 may also incorporate other containment components in addition to or instead of the containment flaps 75. For example, while not shown in the drawings, other suitable containment components may include, but are not limited to, elasticized waist flaps, foam dams in the front, back and/or crotch regions, and the like.

The diaper 21 can also include a surge management layer (not shown) which helps to decelerate and diffuse surges or gushes of liquid that may be rapidly introduced into the absorbent body 53. Desirably, the surge management layer can rapidly accept and temporarily hold the liquid prior to releasing the liquid to the absorbent structure. In the illustrated embodiment, for example, a surge layer can be located between the absorbent body 53 and the bodyside liner 51. Examples of suitable surge management layers are described in U.S. Pat. No. 5,486,166 entitled FIBROUS NON-WOVEN WEB SURGE LAYER FOR PERSONAL CARE ABSOR- BENT ARTICLES AND THE LIKE by C. Ellis and D. Bishop, which issued Jan. 23, 1996, and U.S. Pat. No. 5,490, 846 entitled IMPROVED SURGE MANAGEMENT FIBROUS NON-WOVEN WEB FOR PERSONAL CARE ABSORBENT ARTICLES AND THE LIKE by C. Ellis and R. Everett, which issued Feb. 13, 1996, the entire disclosures of which are hereby incorporated by reference in a manner that is consistent herewith.

To provide improved fit and to help further reduce leakage of body exudates from the diaper 21, elastic components are typically incorporated therein, particularly at the waist area and the leg areas. For example, the diaper 21 of the illustrated embodiment of FIGS. 1 and 2 has waist elastic components 85 and leg elastic components 87. The waist elastic components 85 are configured to gather and shirr the end margins of the diaper 21 to provide a resilient, comfortable close fit around the waist of the wearer and the leg elastic components 87 are configured to gather and shirr the side margins of the diaper at the leg openings 37 to provide a close fit around the wearer's legs.

Examples of other suitable diaper 21 configurations are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., U.S. Pat. No. 5,509,915 issued Apr. 23, 1996 to Hanson et al., U.S. Pat. No. 5,993,433 issued Nov. 30, 1999 to St. Louis et al., and U.S. Pat. No. 6,248,097 issued Jun. 19, 2001 to Beitz et al., the disclosures of which are herein incorporated by reference.

Still referring to FIGS. 1 and 2, the diaper 21 further comprises an elective component in the form of an umbilical cord component, generally indicated at 91. During the first few days or weeks of a newborn baby's life, umbilical cord care is important to prevent irritation of the freshly severed cord. Accordingly, it is important to expose the umbilical cord to ambient air to facilitate the drying and falling off process. Moreover, it is important to prevent urine and feces from coming into contact with the umbilical cord. The umbilical cord component 91 is selectively configurable from a first configuration as shown in FIG. 2 in which the diaper otherwise resembles a conventional diaper to a second configuration as shown in FIG. 3 in which an umbilical relief area 93 of the diaper is formed to accommodate (i.e., reduce the risk of contact of the diaper against) the umbilical cord. For example, until the umbilical cord falls off, the umbilical cord component 91 may be used in its second configuration. Afterwards, the umbilical cord component 91 may be used instead in its first configuration.

In the illustrated embodiment, the umbilical cord component 91 comprises a pair of flaps 95 foldable along respective fold lines 97 formed in the diaper 21 generally diagonal to the longitudinal axis X thereof at the front region 25 of the diaper, and more suitably near the front end 33 of the diaper. In the first configuration of the umbilical cord component 91 as shown in FIG. 3, the flaps 95 are interconnected along a common line of weakness 99 formed in the diaper 21 and extending longitudinally inward from the front end 33 of the diaper. The term "line of weakness" refers to a line along which the diaper 21 is more readily ruptured, or torn, upon application of a tearing force to the diaper. The lines of weakness 99 may be suitably formed by partial pressure cutting, partial ultrasonic cutting, partial thermal deformation, mechanical thinning or other suitable techniques. As an example, a line of weakness 99 may suitably comprise perforations as shown in FIG. 2, a plurality of separation points, a score line, a breakaway line or areas, a chain stitch or other suitable line of weakness.

As used herein "perforation" means one or more holes, slits, apertures, voids, or the like, or combinations thereof through one or more materials to facilitate separation. The perforations may include a line of holes defining a perforated area wherein the holes are separated by intact material or materials defining an intact area. The amount of perforated area relative to the intact area can be altered to change the amount of force required to tear the diaper 21 along the line of weakness 99. A "chain stitch" is a stitch formed in the material such that when an end of the stitching is pulled, the stitch unravels and the material separates.

Each line of weakness 99 can pass partially or completely through the thickness of the diaper 21. Each line of weakness 99 can also be either linear or non-linear in shape or configuration within the scope of this invention. Non-linear shapes can include curved or arcuate profiles, a saw tooth profile, a semi-circular profile, a zigzag profile, a sinusoidal profile, or any other geometrical profile that is not a straight line.

The fold lines 97 may be formed in the diaper 21 by ultrasonic bonding, pressure bonding, thermal bonding, or other processes by which a crease, crimp, hinge or the like is formed, or combinations thereof. The fold lines 97 are adapted to allow the flaps 95 to fold at a desired location and in a desired orientation to form a sufficient umbilical cord relief area 93. The fold lines 97 may also be adapted to make the flaps 95 generally "floppy" in that there is minimal force resisting the flap against movement about the fold lines following tearing of the flaps apart along the line of weakness 99. While not shown in the drawings, it is contemplated that the umbilical cord component 91 may include multiple fold lines 97 that provide a caregiver the ability to customize the size and/or shape of the umbilical relief area 93. It is also understood that the fold lines 97 may be omitted without departing from the scope of this invention.

To selectively configure the umbilical cord component 91 from its first configuration to its second configuration (FIG. 3), the diaper 21 is torn along the length of the line of weakness 99 separating the flaps 95 and the flaps are folded inward at the fold lines 97 to generally tuck the flaps within the diaper and to define the umbilical cord relief area 93 of the diaper at the front region 25 thereof. The flaps 95 may be secured in the tucked position by a suitable flap anchoring system (not shown) . As an example, the flap anchoring system may suitably comprise pockets, fasteners (i.e., hook, loop, buttons, snaps) adhesive, cohesive, or combinations thereof. Absorbent articles having anchoring systems are disclosed in co-assigned U.S. patent application Ser. No. 11/111,531 entitled Diaper With Umbilical Feature, filed Apr. 20, 2005, the entire disclosure of which is incorporated herein by reference.

It is contemplated that the umbilical cord component 91 may comprise more than one line of weakness 99 and more or less than the two fold lines 97 shown in the embodiment of FIGS. 1-3. For example, in one suitable embodiment a sufficient number of lines of weakness 99 may be provided to permit the flap 95 to be entirely separated from the diaper in the second configuration of the umbilical cord component 91. In other embodiments, one or more lines of weakness 99 may be oriented and arranged depending on the desired number of flaps 95 (which may be one, two (as shown in FIG. 3) or more than two) and the desired shape of the flaps and umbilical cord relief area 93 of the diaper 21.

Figure 4:
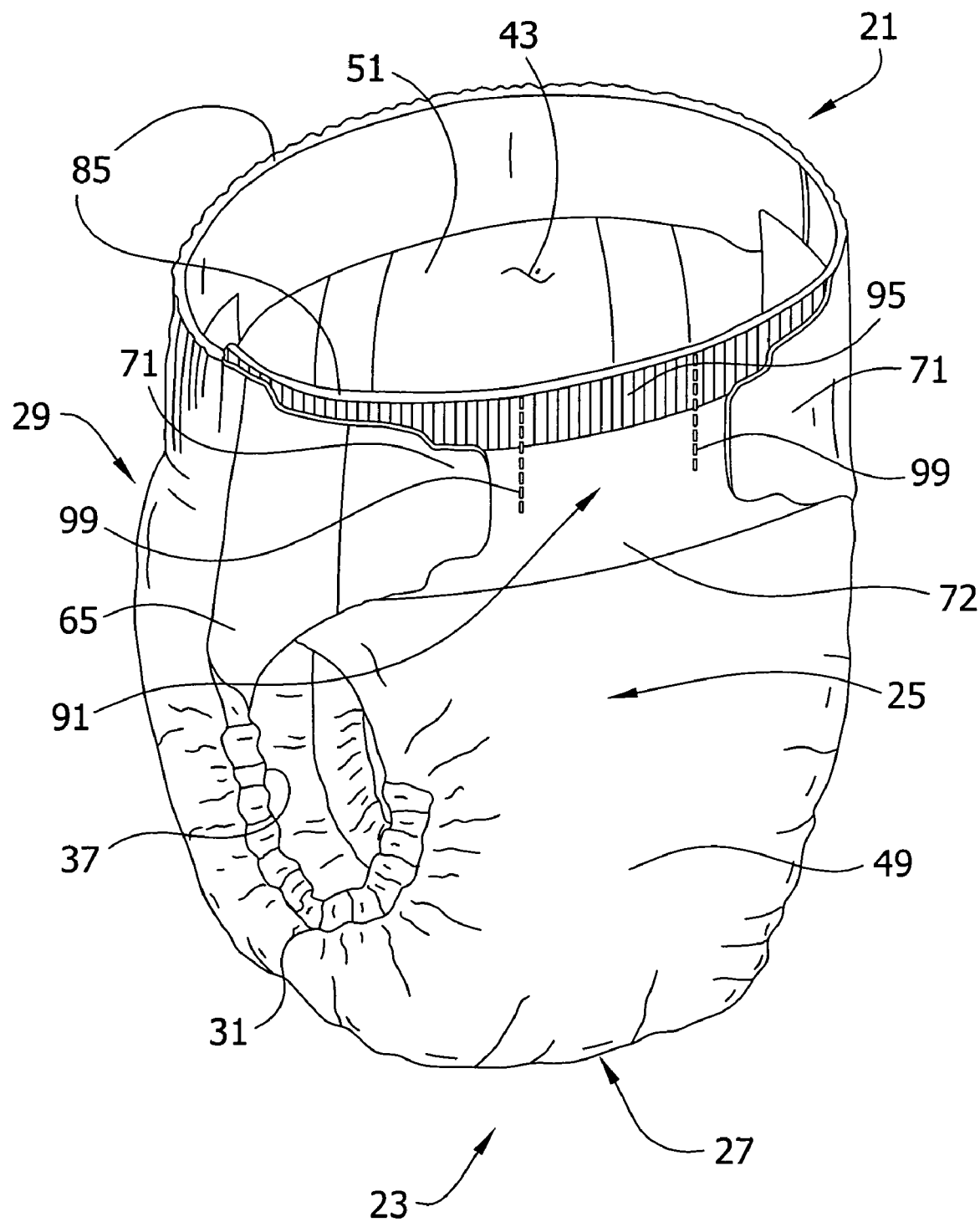
FIG. 4 is a perspective view similar to FIG. 2 illustrating an alternative embodiment of the umbilical cord component, with the umbilical cord component in a first configuration.
Figure 5:
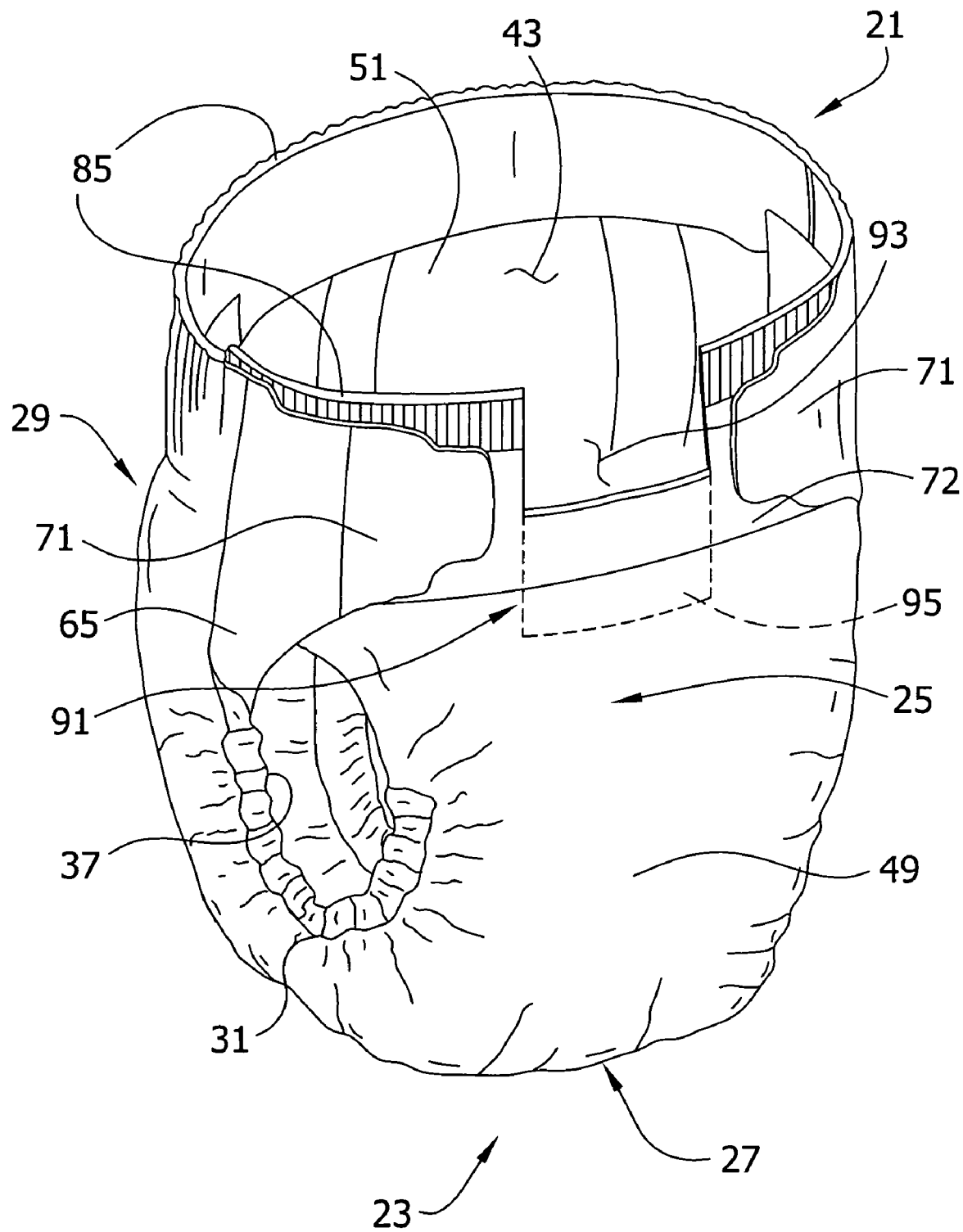
FIG. 5 is a perspective view of the diaper of FIG. 4 with the umbilical cord component in a second configuration for accommodating the wearer's umbilical cord.
Figure 6:
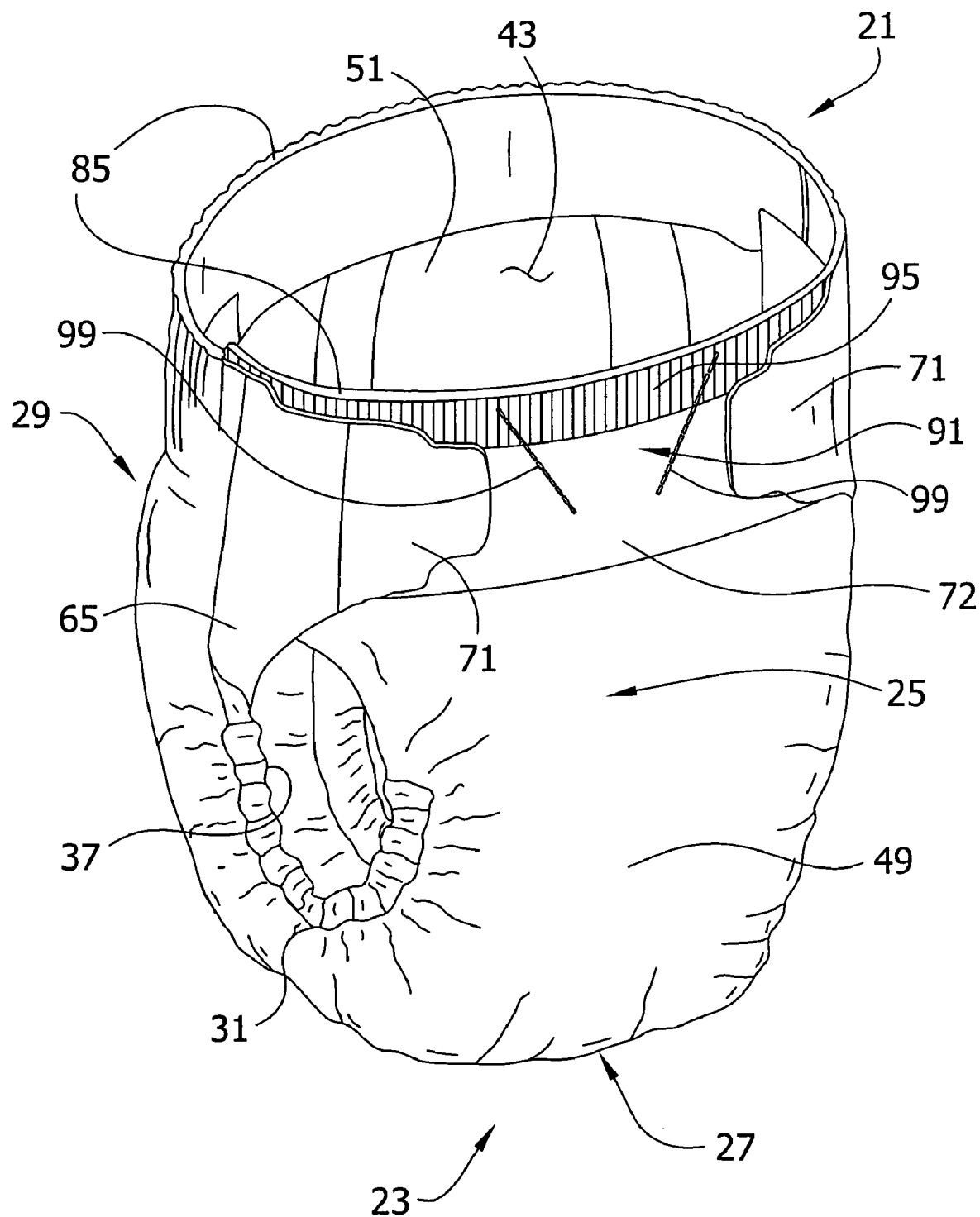
FIG. 6 is a perspective view similar to FIG. 2 illustrating a third embodiment of the umbilical cord component, with the umbilical cord component in a first configuration.
Figure 7:
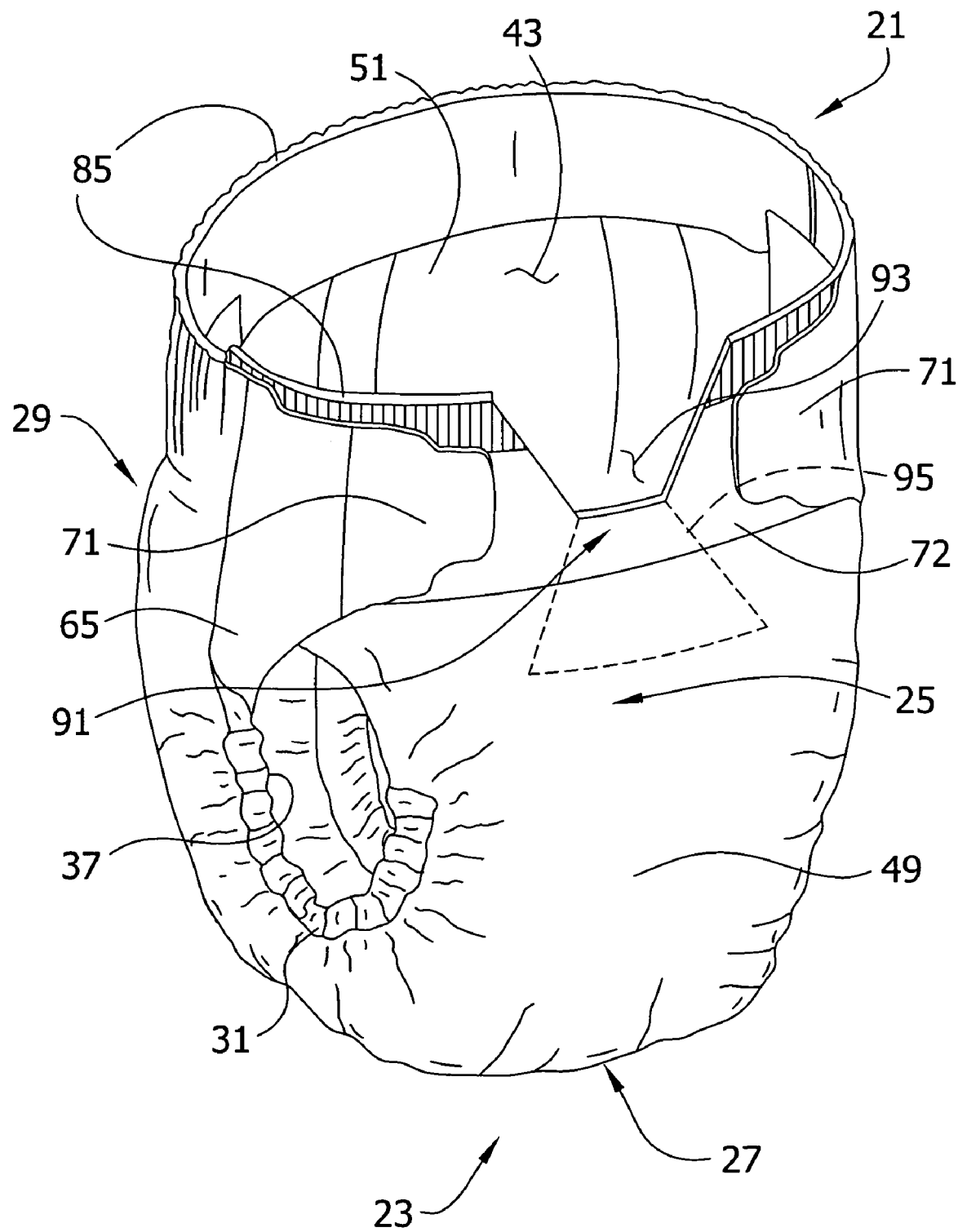
FIG. 7 is a perspective view of the diaper of FIG. 6 with the umbilical cord component in a second configuration for accommodating the wearer's umbilical cord.
Figure 8:
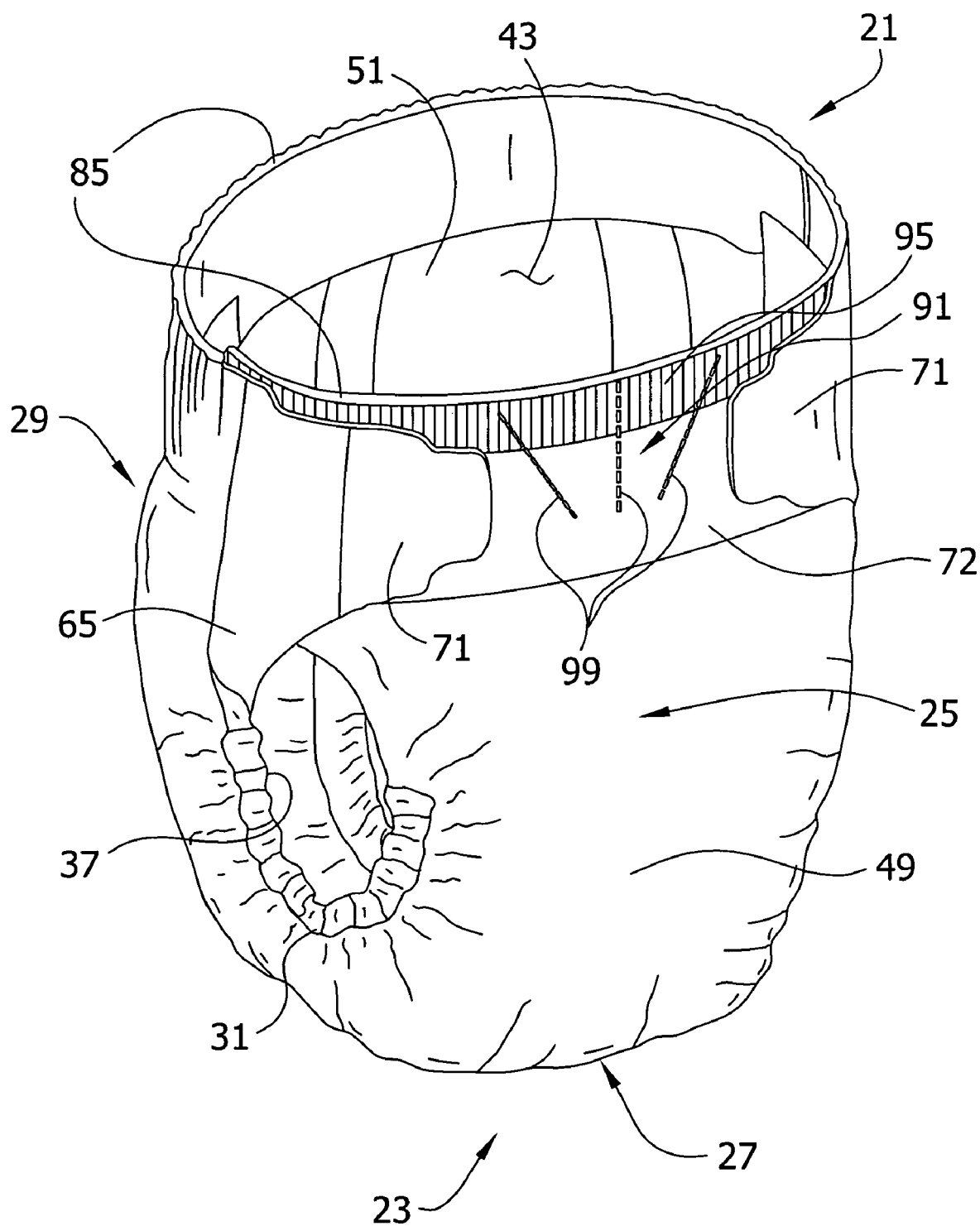
FIG. 8 is a perspective view similar to FIG. 2 illustrating a fourth embodiment of the umbilical cord component, with the umbilical cord component in a first configuration.
Figure 9:
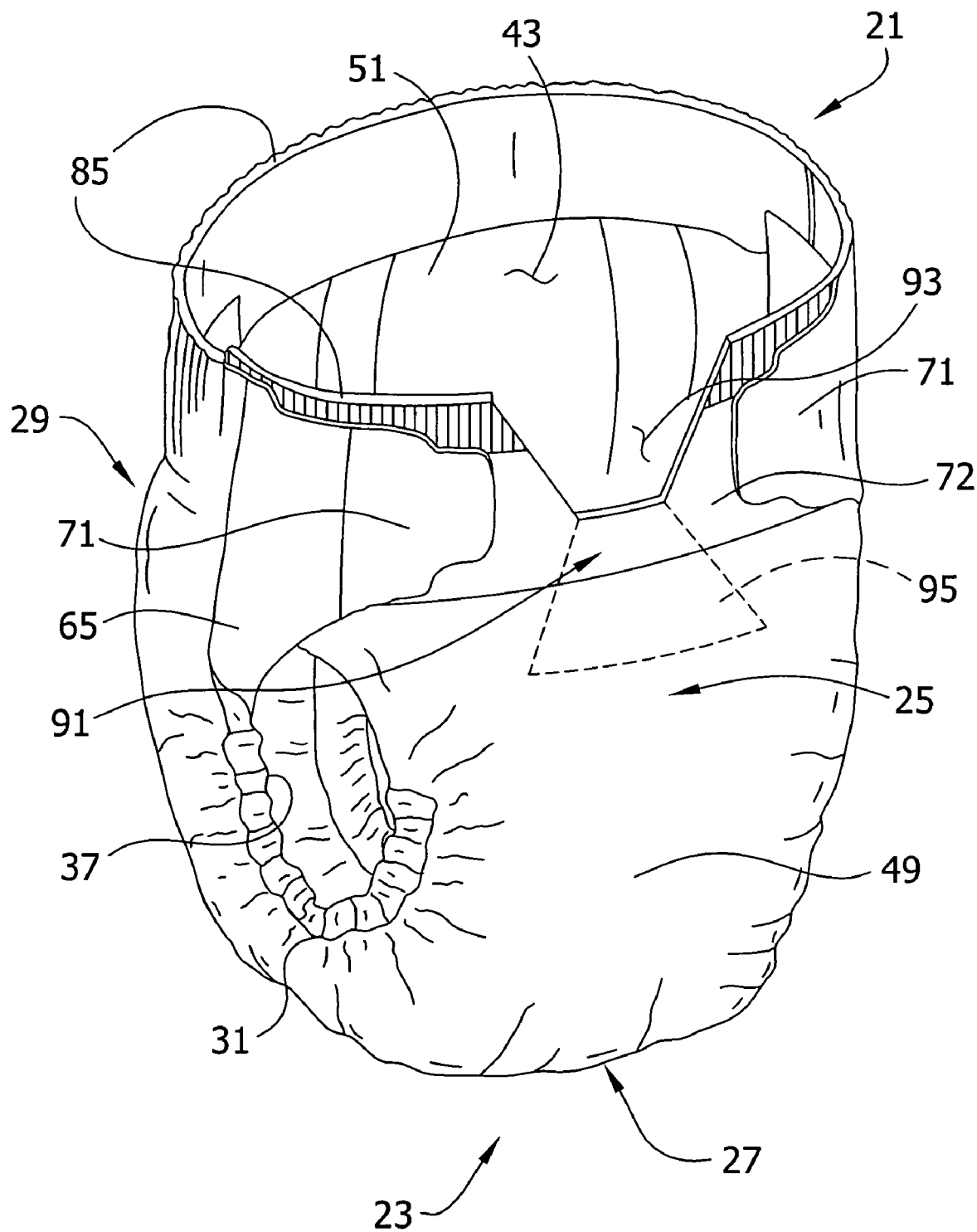
FIG. 9 is a perspective view of the diaper of FIG. 8 with the umbilical cord component in a second configuration for accommodating the wearer's umbilical cord.

For example, FIGS. 4 and 5 illustrate another embodiment in which the umbilical cord component 91 comprises a pair of lines of weakness 99 extending longitudinally from the front end 33 of the diaper 21 in parallel spaced relationship with each other. In the second configuration of the umbilical cord component 91 of this embodiment, the diaper 21 is torn along the lines of weakness 99 and to form a single, rectangular flap 95 that is folded inward of the diaper to accommodate the wearer's umbilical cord. In the embodiment of FIGS. 6 and 7, opposed, generally diagonal lines of weakness 99 are formed in the diaper 21 such that in the second configuration of the umbilical cord component 91 a single, generally trapezoidal flap 95 is formed. FIGS. 8 and 9 illustrate a diaper 21 having an umbilical cord component 91 comprised of three lines of weakness 99, a central, longitudinally extending line of weakness and opposed, generally diagonal lines of weakness, which in the second configuration of the umbilical cord component result in forming a pair of flaps that fold inward of the diaper.

The lines of weakness 99 and/or fold lines 97 of any of the above embodiments may be made more visible or prominent through the use of one or more indicators (not shown), such as by printing, embossing, bonding, or the like, or combinations thereof of one or more indicia proximate the lines of weakness.

FIGS. 10-13 illustrate an embodiment in which the disposable absorbent article is a pants-type absorbent article (broadly, pants), generally indicated at 121, such as children's training pants or an adult incontinence briefs. In pants-type absorbent articles 121, a front waist region 123 is pre-fastened to a back waist region 125 along laterally opposed side seams 127, either releasably (e.g., as by a suitable fastening system) or permanently (e.g., as by bonding, adhesive or other suitable technique) to form a three-dimensional configuration having a waist opening 143 and a pair of leg openings 137 prior to the article 121 being placed on the wearer. Examples of suitable training pants constructions are disclosed in U.S. Pat. No. 6,761,711 issued Jul. 13, 2004 to Fletcher et al., the disclosures of which are incorporated herein by reference. Suitable adult incontinence briefs are disclosed in U.S. Pat. No. 6,497,695 issued Dec. 24, 2002 to Bruemmer-Prestley et al., the disclosures of which are also incorporated herein by reference. The pants 121 have an outer cover 149, bodyside liner 151 and absorbent structure 153 therebetween, which may be constructed of materials similar to those from which the corresponding elements of the diaper 21 are constructed.

Figure 10:
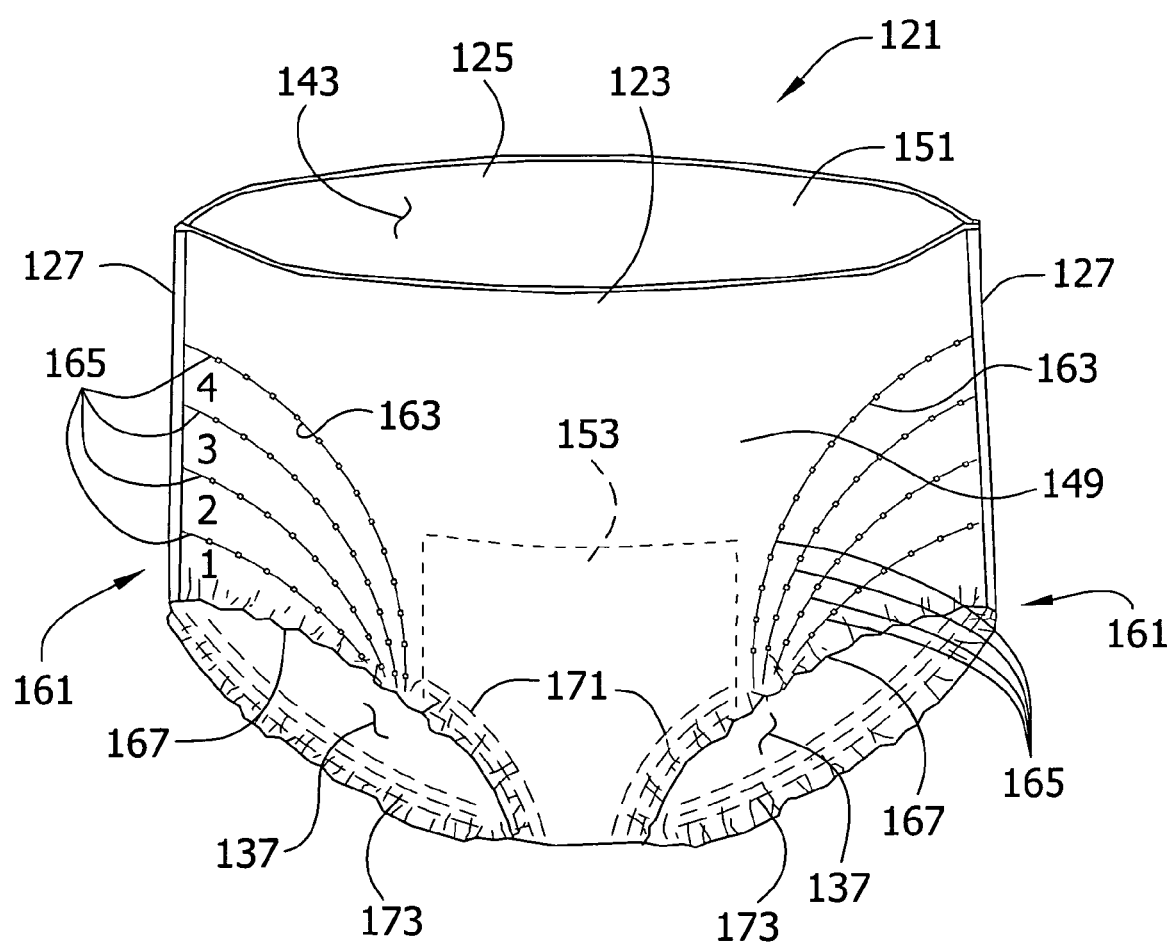
FIG. 10 is a front perspective of a pants-type absorbent article having an elective component in the form of leg opening components, with the leg opening components in a first configuration.
Figure 13:
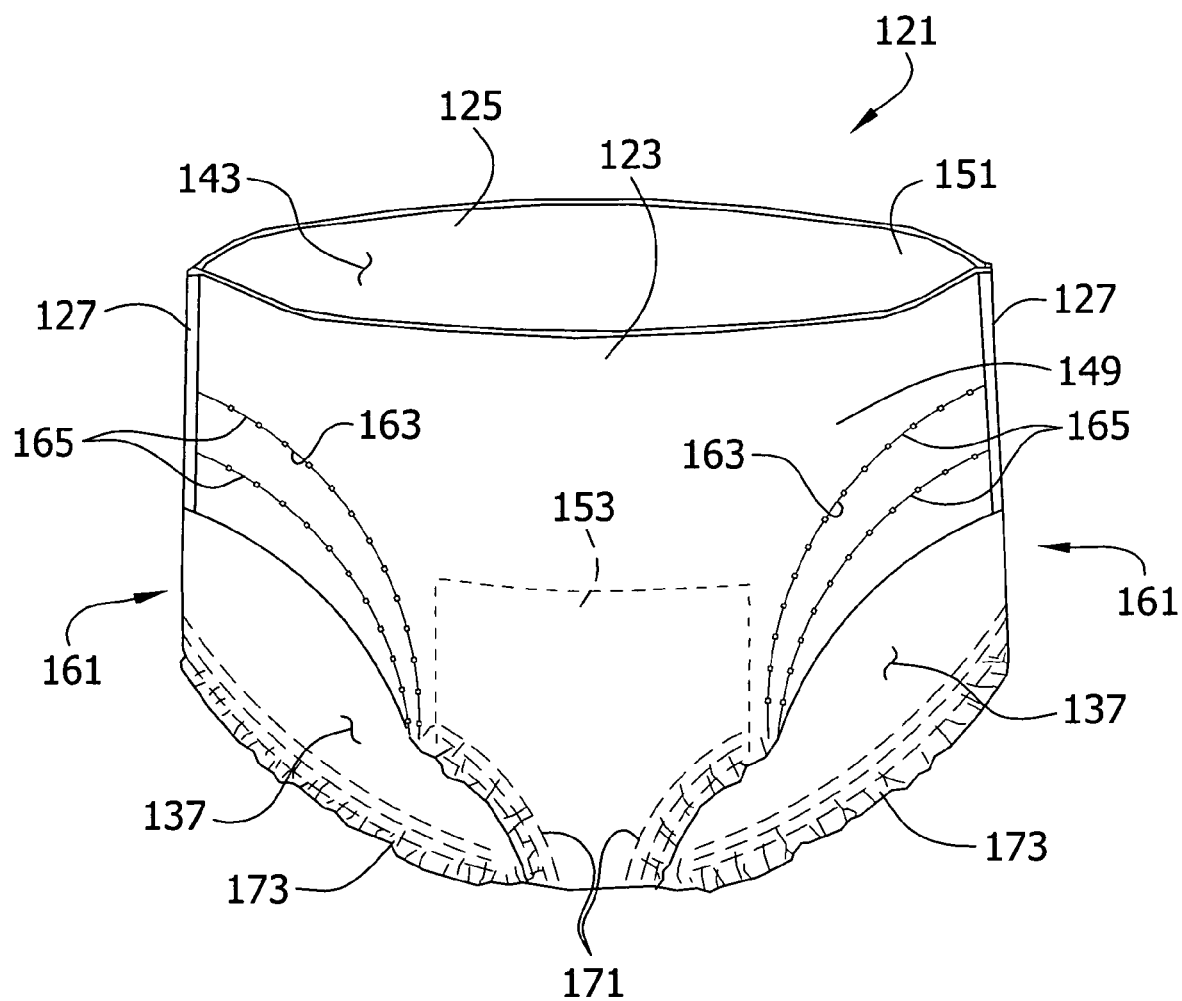
FIG. 13 is a front perspective of the article of FIG. 10 with the leg opening components in a second configuration in which the circumference of each leg opening of the article is increased.

The illustrated pants 121 further comprise an elective component in the form of a pair of leg opening components (i.e., a leg opening component associated with each leg opening of the pants), generally indicated at 161, for selectively adjusting the size (e.g., the circumference) of the leg openings 137 to accommodate the thickness of the wearer's thighs. In particular, the leg opening components 161 are each selectively configurable from a first configuration as shown in FIG. 10 in which the pants 121 otherwise resembles conventional pants to a second configuration as shown in FIG. 13 in which the circumference of each leg opening is increased relative to the circumference of each leg opening in the first configuration of the leg opening components. The leg opening components 161 may alternatively, or additionally, be used to selectively alter the appearance of the pants, e.g., from a brief style appearance in the first configuration of the leg opening components to more of a bikini style appearance in the second configuration thereof. It is also understood that the leg opening components 161 may instead, or may additionally, be provided on diapers and other disposable absorbent articles.

In the illustrated embodiment, each leg opening component 161 is interconnected at an inner edge 163 thereof to the pants along a line of weakness 165 in the first configuration of the leg opening component 161 such that an outer edge 167 of the leg opening component defines the leg opening of the pants. In particular, the leg opening components 161 shown in FIG. 10 each comprise a set of four independent strips, identified as 1, 2, 3 and 4, respectively, from the outermost to the innermost strip. The innermost strip 4 is interconnected to the pants along a line of weakness 165 (e.g. perforations in the illustrated embodiment) and the other strips are interconnected to each other along additional lines of weakness (also perforations in the illustrated embodiment). It is understood, however, that each leg opening component 161 may comprise less than four strips, including a single strip, or more than four strips without departing from the scope of this invention.

Each strip 1-4 of the illustrated embodiment is generally arcuate and extends from the respective side seam 127 to the respective leg opening 137 of the pants 121, with the width of the strip increasing from the leg opening out to the side seam. The lines of weakness 165 in the illustrated pants 121 are spaced from each other along the leg opening 137 and along the side seam 127. However, it is contemplated that the lines of weakness 165 may start at approximately the same point along the leg opening 137 and/or along the side seam 127 and remains within the scope of this invention. The lines of weakness 165 may terminate adjacent to (i.e., short of), at or in the respective side seam 127.

The lines of weakness 165 of the leg opening component 161 each have a different length, with the length increasing from the outermost line of weakness to the innermost line of weakness interconnecting the leg opening component to the pants 121. The strips 1-4 may also have different lengths and may further have different surface areas. For example, the outermost strip 1 may have the smallest surface area with the surface of each strip increasing to the innermost strip 4.

In use, the pants 121 may be placed on the wearer with the pants in the first configuration of the leg opening components 161. If the pants fit too tight around the wearer's thighs, or if the appearance of the pants is desired to be altered, one or more strips are at least in part separated from the other strips, or from the pants, and more suitably completely separated from the other strips or from the pants. Removal of one or more of the strips 1-4 to reconfigure the pants 121 in the second configuration of the leg opening components 161 increases the circumference of each leg opening so that the pants do not fit so tight around the wearer's thighs. Where less than all of the strips 1-4 are removed in the second configuration of each leg opening component 161, the outermost remaining strip at least in part defines the leg opening 137 of the article 121. The strips 1-4 may also, or may alternatively, be removed to provide a more bikini-type appearance to the pants 121. It is also contemplated that the strips may be separated from the pants 121 prior to the pants being placed on the wearer.

Figure 11:
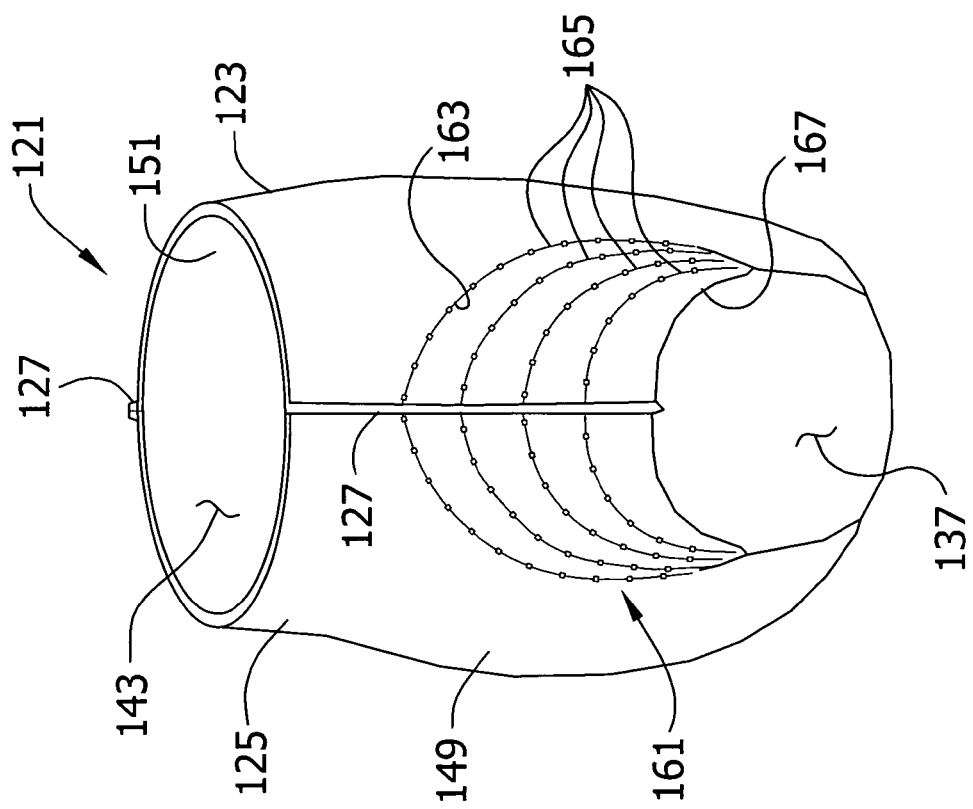
FIG. 11 is a side elevation of the article of FIG. 10.
Figure 12:
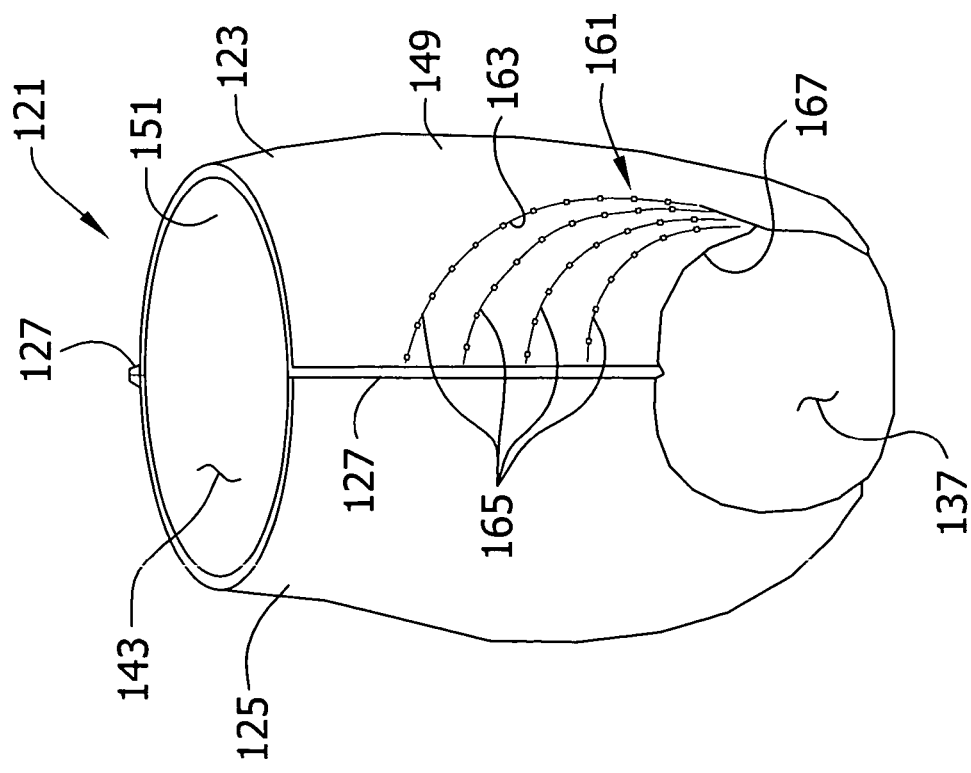
FIG. 12 is a side elevation similar to FIG. 11 but illustrating an alternative embodiment of the leg opening components, with the leg opening components in a first configuration.

It is also contemplated that where more than one strip 1-4 of a respective multi-strip leg opening component is separated from the pants 121, the strips of a respective leg opening component 161 can be disconnected from the pants 121 either sequentially or simultaneously. In the illustrated embodiment the separable strips 1-4 extend from the leg opening 137 to the side seam 127 only in the front waist region 123 of the pants 121. However, the strips 1-4 may be disposed on the back waist region 125 of the pants 121 as shown in the embodiment of FIG. 11, on both the front waist region 123 and the back waist region of the pants as shown in the embodiment of FIG. 12, or continuous strips extending about all or part of the leg opening in both the front and back regions.

With reference again to FIG. 10, the four removable strips 1-4 are all located in the front waist region 123 but crotch elastics 171 and leg elastics 173 do not extend around essentially the entire circumference of each of the leg openings 137. Instead, the elastic strands forming the leg elastic 173 extend from one of the side seams 127 inward toward the longitudinal axis X but they stop short of the crotch elastics 171. One can see that no leg elastics 173 are present in the strips along the circumference of the leg opening 137. This is by design. In FIG. 10, the line of weakness 165 are also spaced away from the crotch elastics 171 and the leg elastics 173. By doing so, it may make it easier for the user to initiate breaking the line of weakness 165. The absence of leg elastics 173 in the front region 123 will not materially affect the function of the pants 121 if the pants are formed at least in part from an elastomeric material. It should be noted that one can align and secure one or more elastic strands (not shown) along each of the lines of weakness 165 so that as one or strips are removed, elastic strands will still be present around the entire leg opening 137.

As explained above, the leg opening components 161 function to enable the user to remove and discard one or more strips to customize the fit of the pants 121 to the user's anatomy. For example, two adults suffering from incontinence may both wear a medium sized incontinence garment. One of the wearers may have larger thighs than the other. In this case, the user with the larger thighs could detach one or more strips 1-4. Detachment of the strips 1-4 causes the leg opening 137 to have a greater circumference and make the pants 121 more comfortable for the wearer with larger thighs. By removing one or more of the strips 14 from the pants 121, one can enlarge the leg openings 137 and also reduce the full side or hip coverage of the user's torso when such is not warranted. For example, on a very hot or muggy day, the user may feel more comfortable when a greater percentage of the pants 121 are removed.

Figure 14:
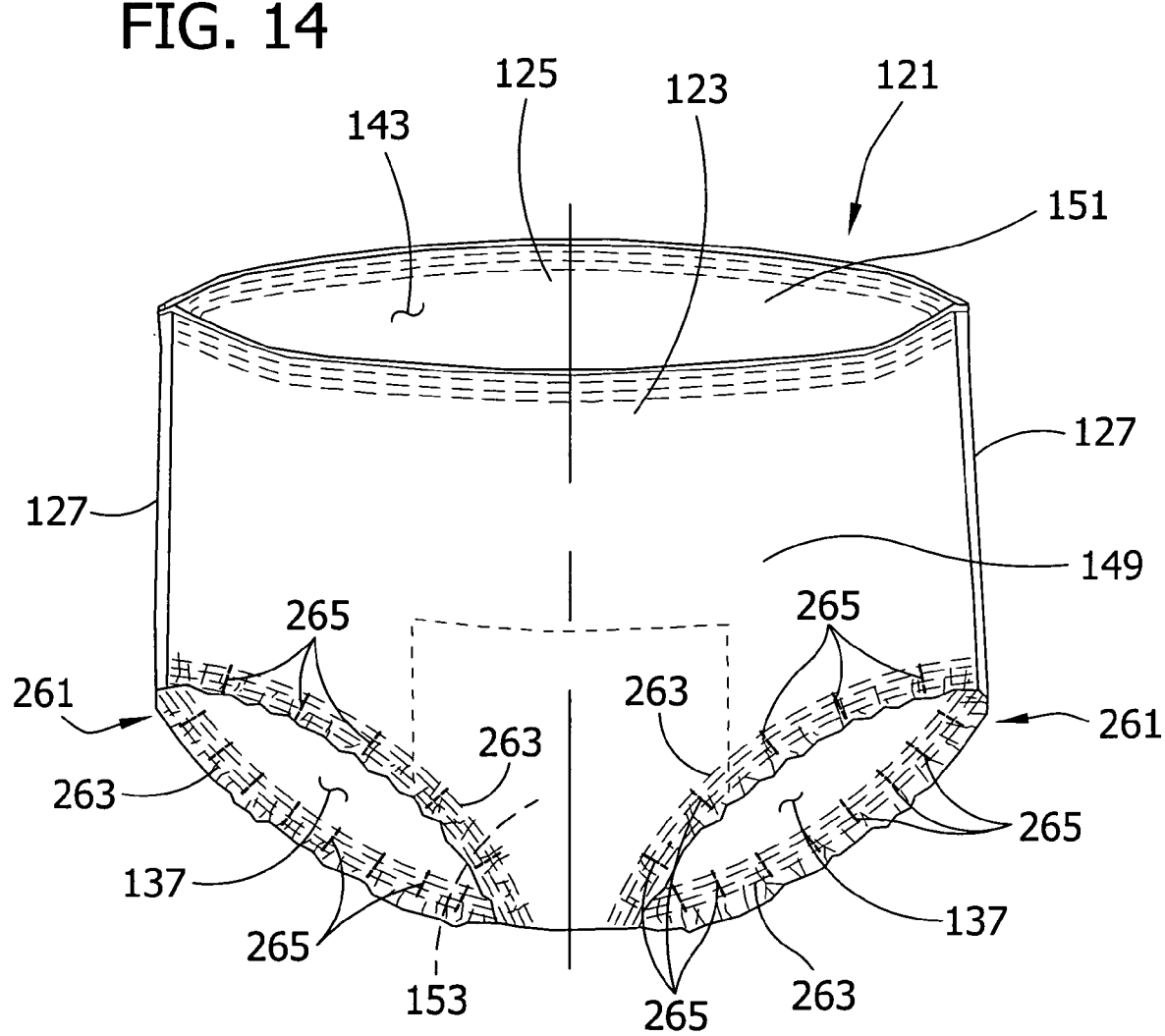
FIG. 14 is a front perspective similar to FIG. 10 illustrating a third embodiment of the leg opening components, with the leg opening components in a first configuration.
Figure 15:
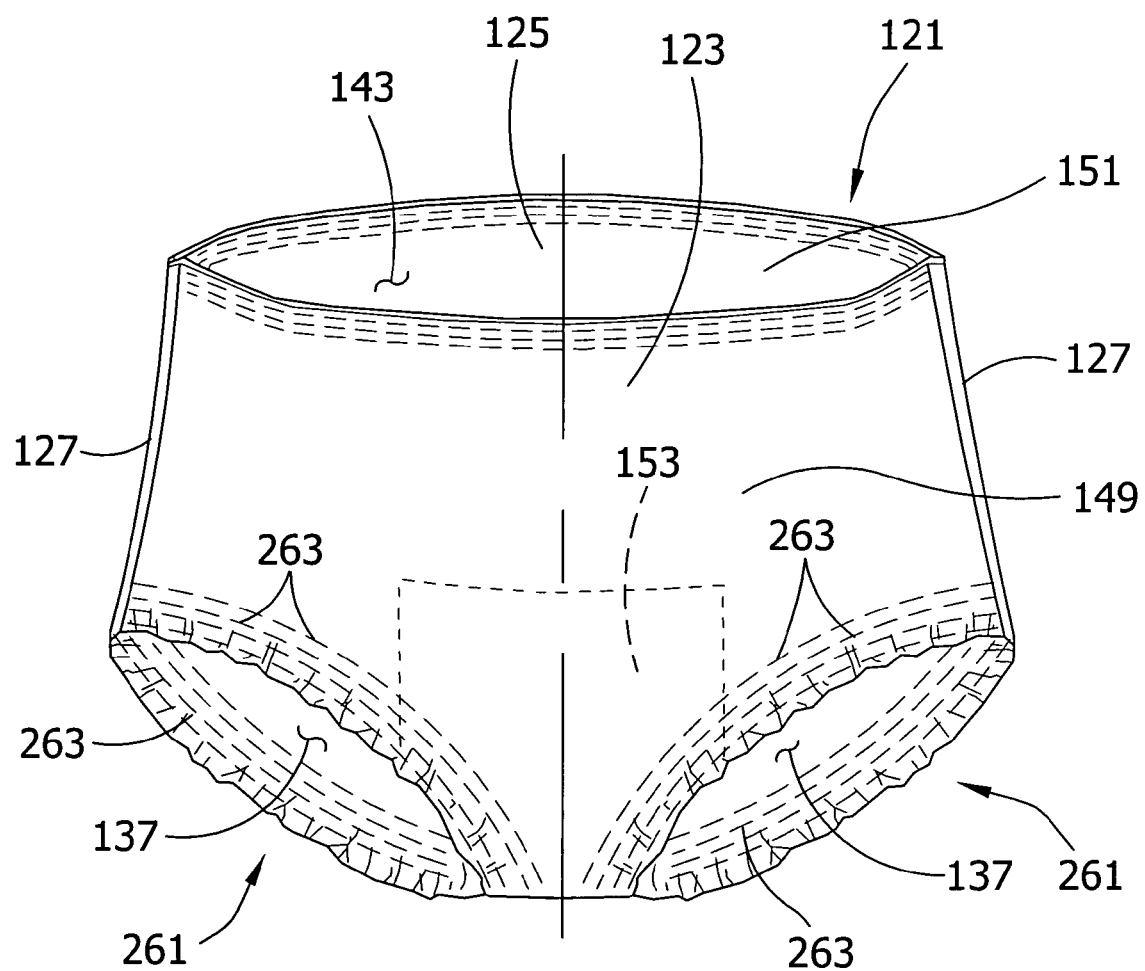
FIG. 15 is a front perspective of the article of FIG. 14 with the leg opening components in a second configuration in which the circumference of each leg opening of the article is increased.

In another embodiment illustrated in FIGS. 14-15, leg opening components, generally indicated at 261, of the pants 121 comprise rupturable elastic strands 263 positioned adjacent the leg openings 137 and secured between the bodyside liner 151 and the outer cover 149 of the pants. Details regarding the construction of absorbent articles with elastic strands that may be modified to be rupturable at intermittent locations along its length may be found, for example, in U.S. Pat. No. 6,497,696, "Refastenable Absorbent Article Exhibiting Improved Body Fit," issued Dec. 24, 2002 to Freiburger et al. and in U.S. Pat. No. 6,702,798, "Folded Absorbent Article," issued Mar. 9, 2004 to Christoffel et al., which are incorporated herein by reference in their entireties.

In the illustrated embodiment of FIG. 14, four elastic strands 263 are disposed adjacent to and substantially encircle each of the leg openings 137, although fewer or more than four elastic strands may be used. It is also understood that the elastic stands 263 may extend only about a portion of the circumference of each leg opening 137. The elastic strands 263 are suitably stretched prior to being secured between the bodyside liner 151 and the outer cover 149 and then allowed to relax after securement, resulting in gathering of the bodyside liner and outer cover into a "puckered" or "gathered" state that can stretch under stress.

At least one of the elastic strands 263, and in the illustrated embodiment all four elastic strands, has at least one, and more suitably two or more lines of weakness 265, illustrated as dashed lines extending generally perpendicular to the elastic strands 263, that create preferential locations at which the elastic strands rupture. As an example, one way to form the lines of weakness 265 is to perforate the elastic strands 263. It is understood that the number and location of lines of weakness 265 can be altered to achieve the desired maximum leg gasketing force. It is further understood that not all of the strands 263 need to have lines of weakness 265. The elastic strands 263 are suitably adhesively attached along their length to the bodyside liner 151 and/or outer cover 149 so as to remain in place even after they are ruptured. As a result, the individual elastic strand segments remaining following rupture remain functional to provide some leg gasketing force but with reduced discomfort to the wearer.

In use, the elastic strands 263 are generally stretched about the wearer's thighs and apply a gasketing force against the wearer's thighs to inhibit leakage from the pants 121. Since not all users have the same size legs, a leg opening that may fit one user well might feel too tight on another user. When a maximum gasketing force is applied to the wearer's legs (i.e., when the elastic strands are stretched beyond a predetermined amount), the elastic strands 263 rupture at one more locations along their length to reduce the tension and allow the circumference of each leg opening 137 to be increased. FIG. 14 illustrates the pants in a first configuration of the leg opening components 261 wherein the elastic strands 263 are in an unruptured condition such that the pants 121 substantially resemble conventional pants, and FIG. 15 illustrates the pants in a second configuration of the leg opening components wherein at least one of the elastic strands has been ruptured. Alternatively, the leg opening 137 of the pants 121 may be manually expanded to rupture the elastic strands 263 prior to trying to fit the pants on the wearer.

Figure 16:
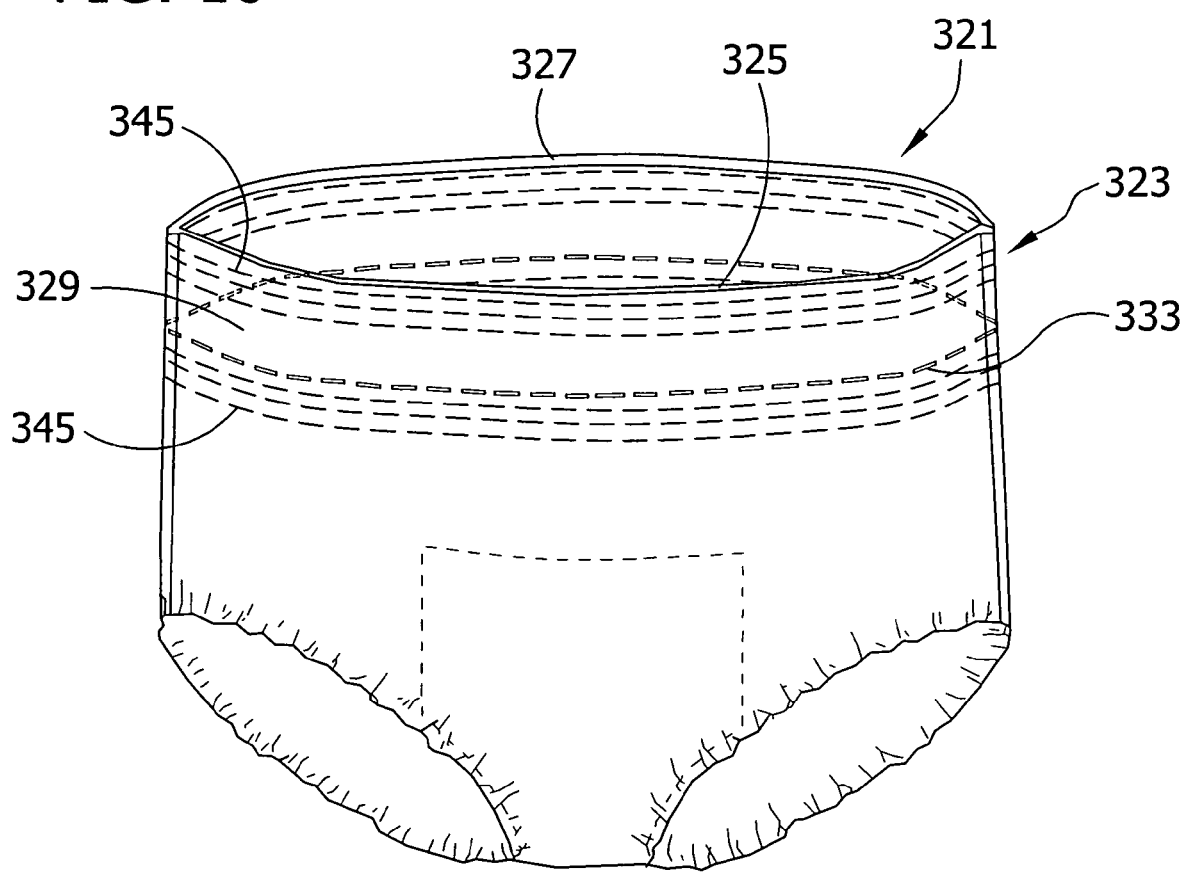
FIG. 16 is a front perspective of a pants-type absorbent article having an elective component in the form of a waist line component, with the waist line component being in a first configuration.

FIGS. 16-20 illustrate a pants-type disposable absorbent article, indicated generally at 321, similar to that of the previous embodiment but instead having an elective component in the form of a waist line component, indicated at 323, for selectively adjusting the relative height of a front waist end 325 and/or back waist end 327 of the pants 321. The rise of an absorbent article such as pants 321 refers herein to the distance from the wearer's navel to the small of the back, as measured through the crotch area. For some users the preferred rise of the article is such that the front waist end 325 of the pants 321 extends to or above the wearer's navel. But others prefer a lower rise to accommodate short-waists and/or low-rise clothing styles, for comfort reasons, for appearance reasons or otherwise. In particular, the waist line component 323 is selectively configurable from a first configuration as shown in FIG. 16 in which the waist line component defines the front and back waist ends 325, 327 of the pants 321 to a second configuration (not show but similar to the second configuration of the waist line component of FIG. 18 described later herein) in which the front and back waist ends of the pants are at a lower position on the wearer than in the first configuration of the waist line component. Stated another way, the length of the pants 321 in the longitudinal direction thereof is greater in the first configuration of the waist line component 323 than in the second configuration thereof.

In the illustrated embodiment of FIG. 16, the waist line component 323 comprises a generally continuous strip 329 extending about the entire waist opening (i.e., the front and back waist ends 323, 325) of the pants 321 and being interconnected to the pants at an inner edge 331 of the waist line component 323 along a line of weakness 333 to define the first configuration of the waist line component. The line of weakness 333, comprised of a line of perforations in the illustrated embodiment, may be otherwise formed by any of the techniques set forth previously. To reduce the length of the pants 321, i.e., to lower the waist line of the pants, the strip 329 is separated from the pants along the line of weakness 333 to define the second configuration (not shown) of the waist line component 323.

Alternatively, the waist line component 323 may comprise a pair of strips 329, one interconnected to the front of the pants 321 and the other interconnected to the back of the pants such that only part of the waist line component may be separated from the pants, e.g., the front strip may be separated from the pants while the back strip remains interconnected, or vice versa, in the second configuration of the waist line component. It is also understood that the width of the strip 329 may be greater or less than that illustrated in FIG. 16 and remain within the scope of this invention.

Figure 17:
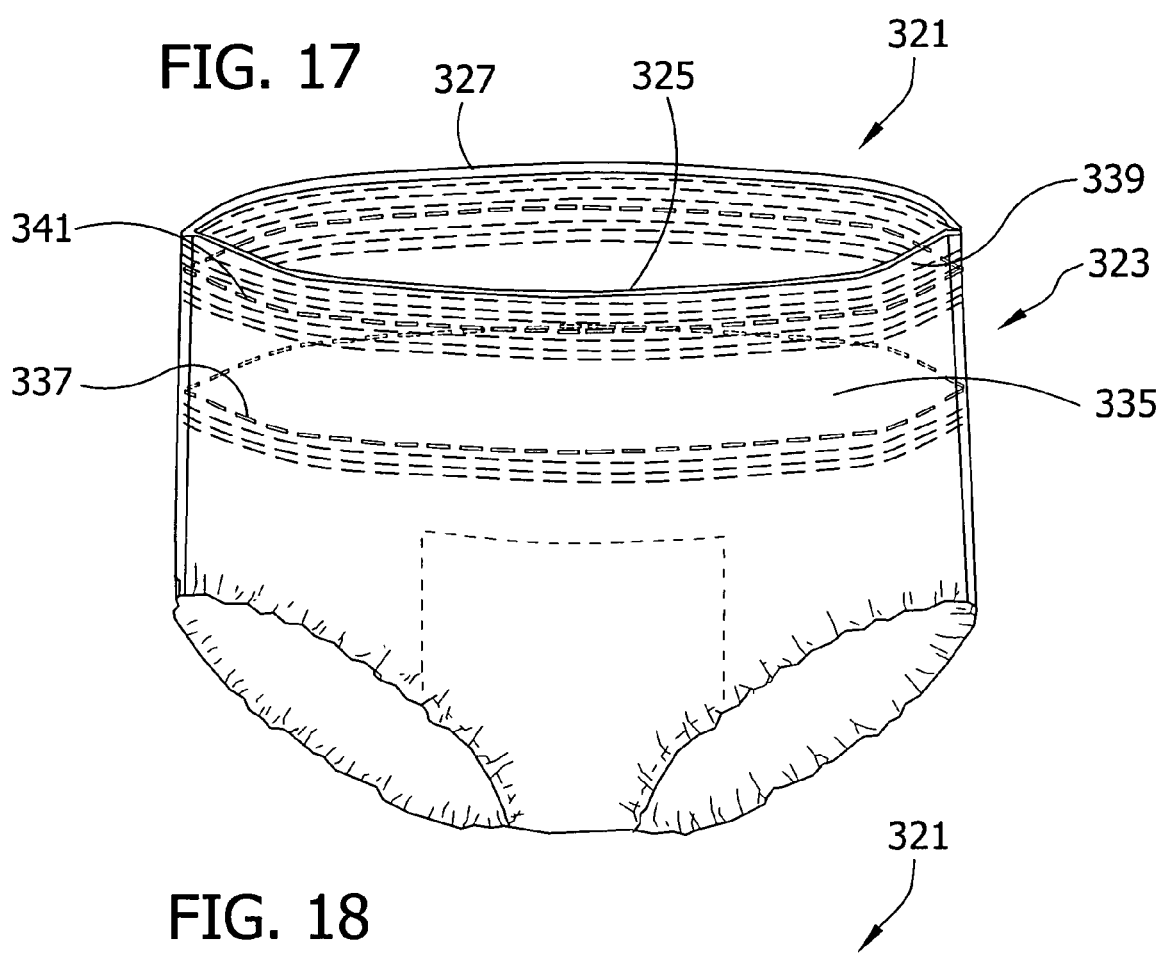
FIG. 17 is a front perspective of the article of FIG. 16 with the waist line component in a second configuration in which the rise of the waist line of the article is lower.
Figure 18:
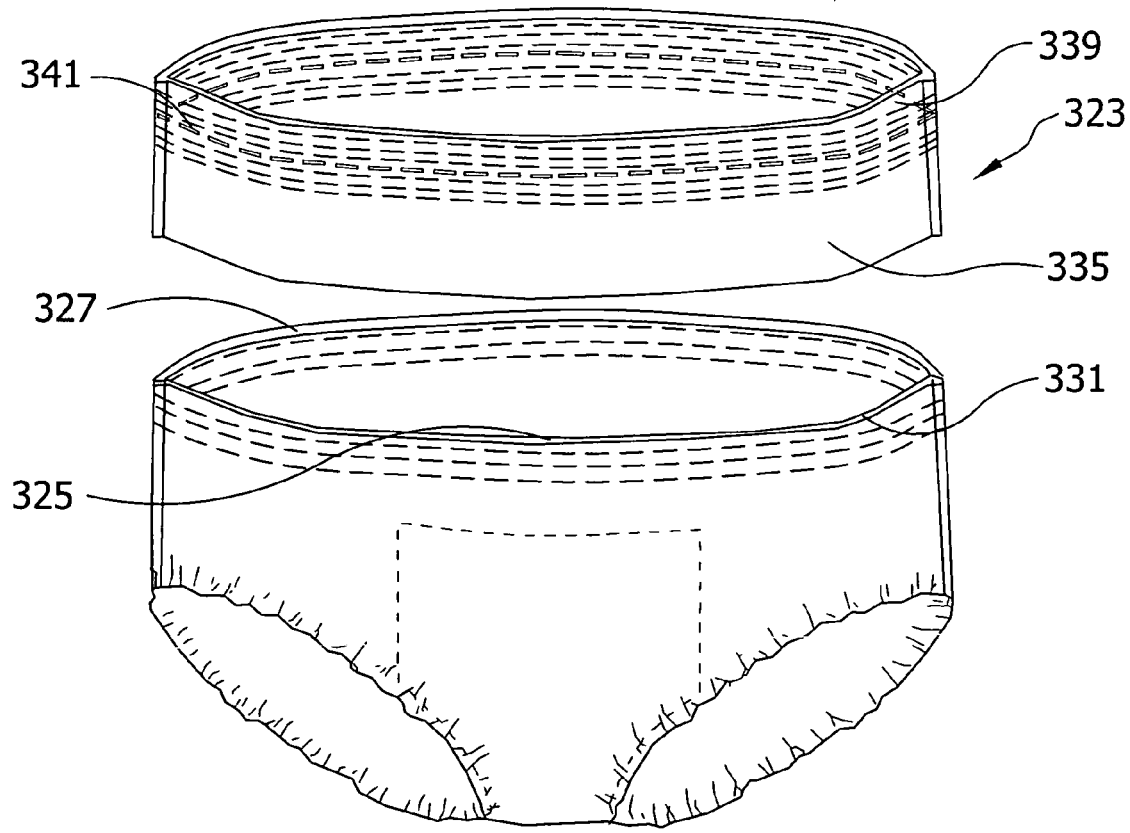
FIG. 18 is a front perspective of the article of FIG. 16 with the waist line component in an alternative second configuration in which the rise of the waist line of the article is further lowered.

In another embodiment, illustrated in FIGS. 17 and 18, the waist line component 323 comprises a pair of strips wherein in the first configuration of the waist line component a longitudinally inner strip 335 is interconnected to the pants 321 about the circumference of the waist of the pants along a first line of weakness 337, and a longitudinally outer strip 339 is interconnected to the inner strip about the circumference of the pants along a second line of weakness 341. In use, the inner and outer strips 335, 339 may be separated from the pants 321, either simultaneously or separately, along the first line of weakness 337 such that in this second configuration (FIG. 18) of the waist line component 323 the inner edge 331 of the pants defines the front and back waist ends 325, 327 of the pants 321. Alternatively, the outer strip 339 may be separated from the inner strip 335 along the second line of weakness 341 to alter the rise of the waist in the second configuration of the pants. It is contemplated that waist line component 323 may instead comprise more than two strips. It is also contemplated that the width of the inner strip 335 may be different from that of the outer strip 339, such as the width of the inner strip being greater than that of the outer strip as in the illustrated embodiment, or vice versa, or the strips may be of equal width.

It is further contemplated that the waist line component 323 may comprise a first, inner pair of strips, with one strip interconnected to the front of the pants 321 and the other interconnected to the back of the pants, and a second, outer pair of strips, with one strip interconnected to the front inner strip and the other interconnected to the back inner strip. This allows different configurations between the front and back waist lines, such as where both the inner and outer strips are separated from the front of the pants 321 while only the outer strip is separated from the back of the pants in the second configuration of the waist line component.

The lines of weakness 333 may be made more visible or prominent through the use of one or more line of weakness indicators (not shown), such as by printing, embossing, bonding, or the like, or combinations thereof or one or more indicia proximate the lines of weakness. The lines of weakness indicators are adapted to draw the caregiver's attention to the lines of weakness 333 and may include shapes, symbols, text, graphics, or the like, or combinations thereof.

The removable strips 335, 339 of the waist line component extend, at least in part, about the waist opening of the pants 321 and, as a result, may include elastic strands 345. Elastic strands 345 are used to secure the pants 321 around the waist of the wearer. As shown in FIGS. 17 and 18, sets of three elastic strands 345 are located adjacent each of the lines of weakness 333 such that when a removable strip 335, 339 is removed, at least one of the sets of elastic strands 345 are positioned to secure the pants 321 around the waist of the wearer. It is understood that the pants 321 can have more or less sets of elastic strands 345 and that each set of elastic strands can have more or less than three strands.

Figure 19:
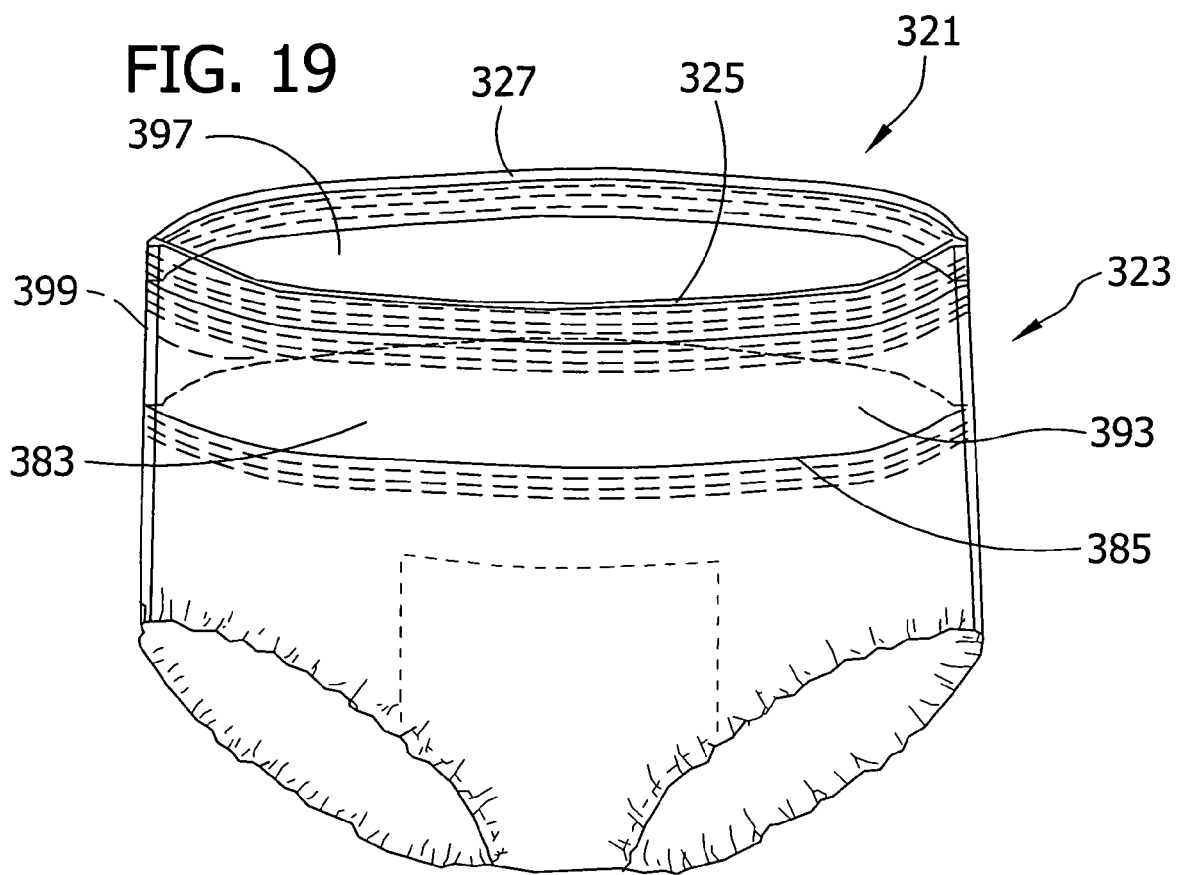
FIG. 19 is a front perspective of a pants-type absorbent article having an alternative embodiment of a waist line component, with the waist line component in a first configuration.
Figure 20:
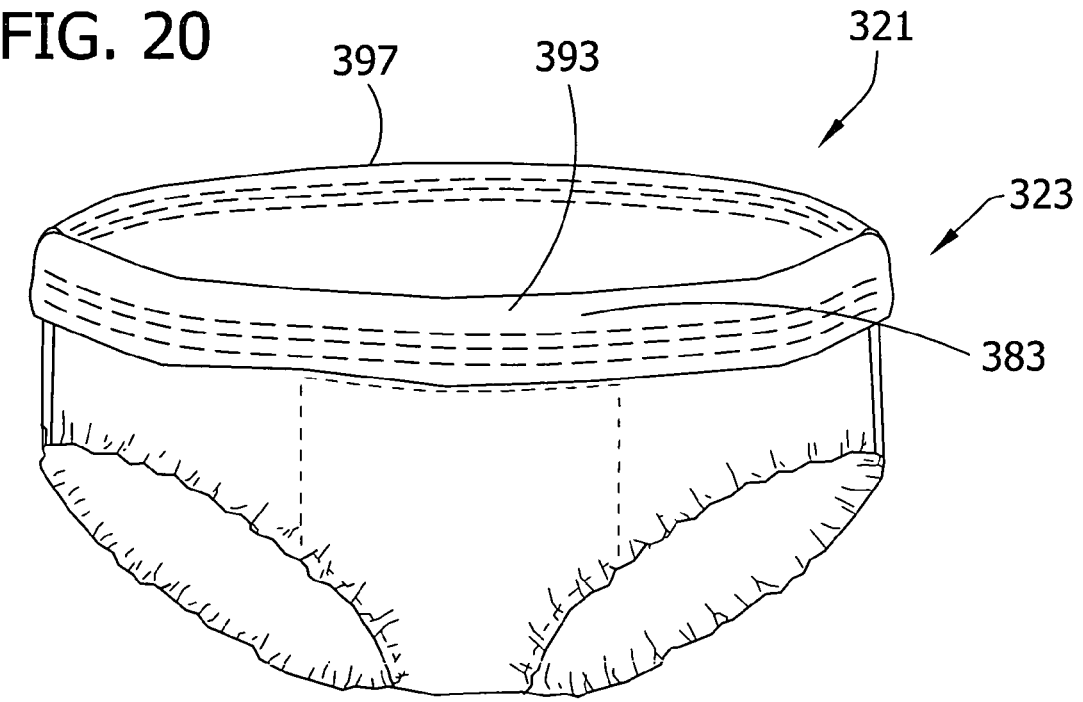
FIG. 20 is a front perspective of the pants of FIG. 19 with the waist line component in a second configuration in which the rise of the waist line of the article is lower.

FIGS. 19-20 illustrate another embodiment in which the waist line component 323 comprises a foldable portion 383 extending about the circumference of the pants 321 generally at the front and back waist ends 325, 327 thereof, and a fold line 385 delineating the foldable portion from the rest of the pants. The fold line 385 may be suitably formed by ultrasonic bonding, pressure bonding, thermal bonding, or other processes by which a crease, crimp, hinge or the like is formed, or combinations thereof. In the first configuration of the waist line component 323, the foldable portion 383 of the pants 321 is unfolded to provide a relatively higher rise of the waistline. To reduce the rise, the foldable portion 383 is folded along the fold line 385 to the second configuration of the waist line component 323 either outward and down over the pants 321 as illustrated in FIG. 20 or inward and down over the pants within the interior of the pants.

It is contemplated that only the foldable portion 383 and fold line 385 may extend about the front of the pants 321 and that the foldable portion may be foldable to the second configuration of the waist line component 323 independent of the back waist end 327 of the pants so that in the second configuration of the waist line component only the rise of the front waist end 325 of the pants is lowered. It is alternatively contemplated that the waist line component 323 may comprise a front foldable portion 393 and corresponding fold line 395 extending transversely across the front region of the pants 321 and a back foldable portion 397 and corresponding fold line 399 independent of the front foldable portion and fold line and extending transversely across the back region of the pants. In such an embodiment, in the second configuration of the pants either the front foldable portion 393 may be folded, or the back foldable portion 397 may be folded, or both the front and back foldable portions may be folded.

It is also understood that the waist line component 323 may comprise two or more fold lines 385 extending transversely of the pants in longitudinally spaced relationship with each other to permit selective folding of the foldable portion 383 at one of the fold lines depending on the desired decrease in rise of the pants waist line. It is also understood that the foldable portion 383 may be folded in the first configuration of the waist line component 323 and then unfolded to increase the rise of the pants 321 waist line in the second configuration of the waist line component.

The pants 321 may also include an anchor system (not shown) for holding the foldable portion(s) 383 of the waist line component 323 in the folded position. As an example, the anchor system may suitably comprise pockets, fasteners (e.g., hooks, loops, buttons, snaps), adhesive, cohesive, or combinations thereof. Absorbent articles having suitable anchoring systems are disclosed in co-assigned U.S. patent application entitled Diaper With Umbilical Feature (attorney docket K-C 21007), filed, the entire disclosure of which is incorporated herein by reference.

In some embodiments, the foldable waist portion 383 may further include one or more folding guides (not shown). These folding guides are adapted to assist the caregiver in locating the fold lines 385 and or selecting the proper fold line to utilize. The folding guides may include printing, embossing, bonding, or the like and combinations thereof. The folding guides may include text, figures, graphics, arrows, symbols, and the like and combinations thereof.

While the waist line component 323 is illustrated in FIGS. 16-20 in association with a pants-type disposable absorbent article, it is understood that the waist line component may be incorporated in a diaper or other non-pants-type disposable absorbent article without departing from the scope of this invention.

Figure 21:
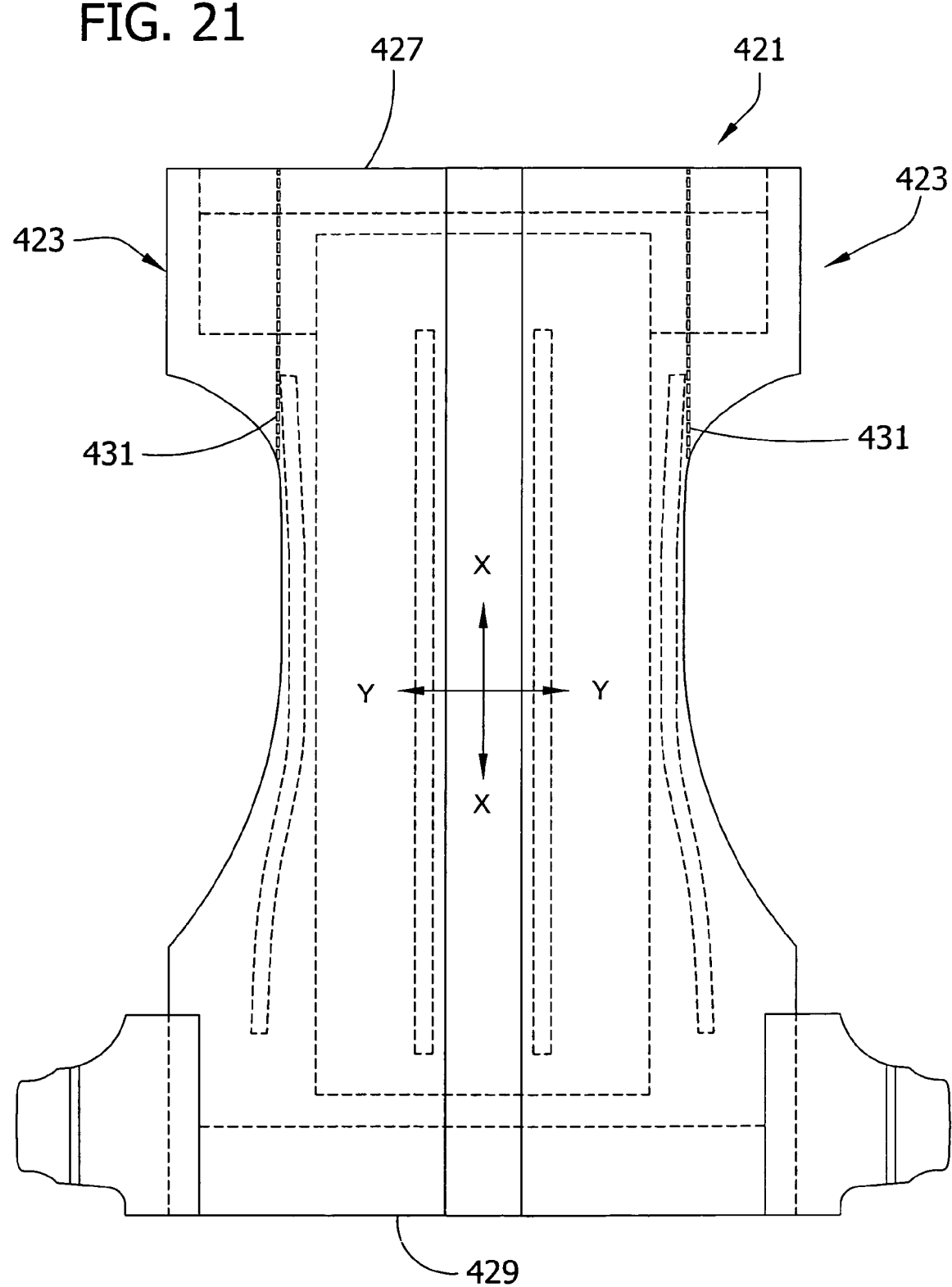
FIG. 21 is a is top plan view of a diaper in an unfastened and laid flat condition and having an elective component in the form of a transverse waist line component, with the transverse waist line component in a first configuration.
Figure 22:
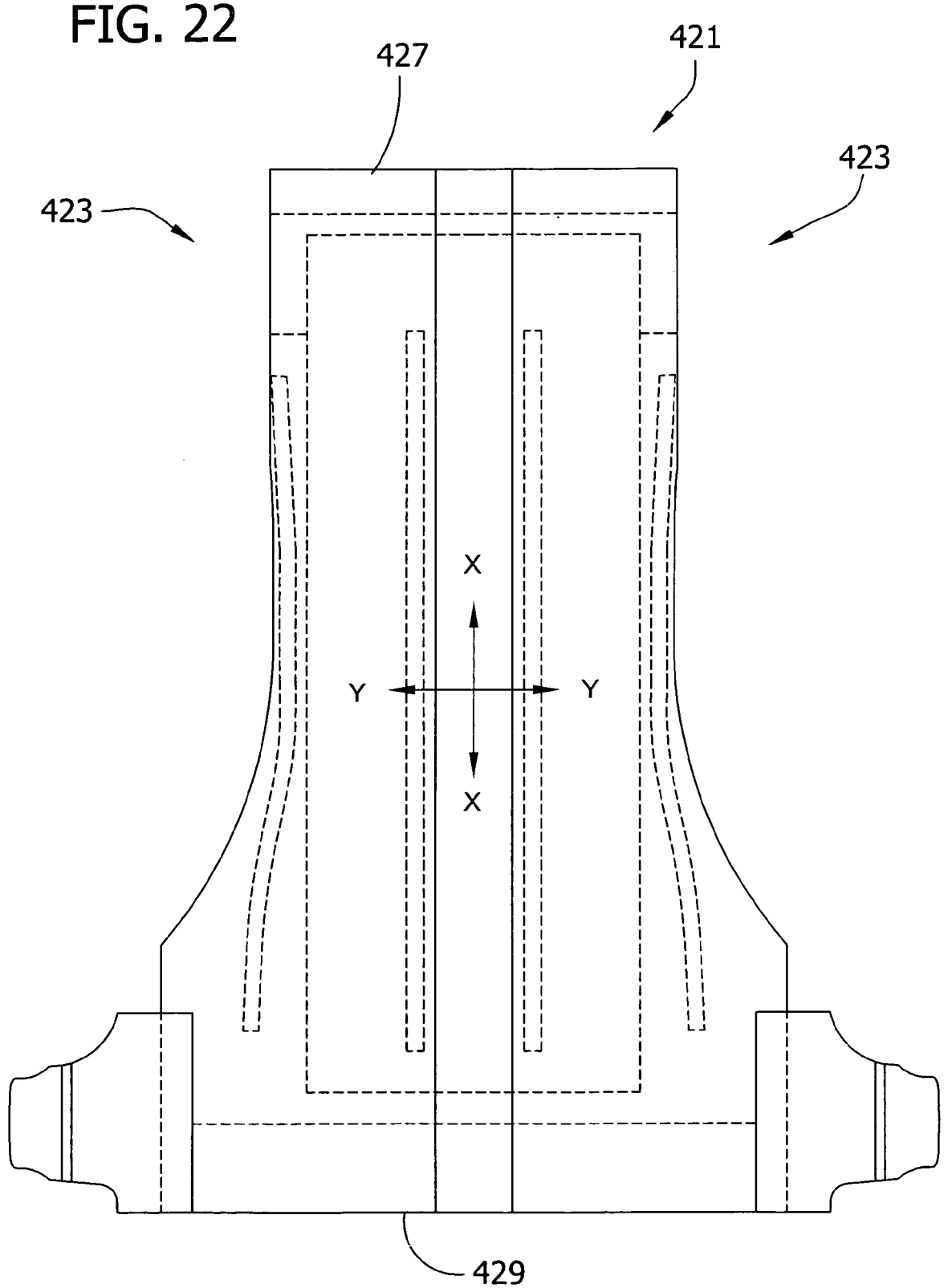
FIG. 22 is a top plan view of the diaper of FIG. 24 with the transverse waist line component in a second configuration in which the width of the diaper at the component is decreased.

FIGS. 21-22 illustrate a diaper, generally indicated at 421, similar to the diaper 21 of FIGS. 1 and 2, but without the umbilical cord component 91. In this embodiment, an elective component of the diaper is in the form of a pair of transverse waist line components, indicated at 432, that allow selective adjustment of the width of a front region 425 of the diaper 421, and more suitably a front waist end 427 of the diaper. Some parents prefer the large hip coverage that a wider front waist end 427 provides when overwrapped by a back waist end 429 during fastening of the diaper 421 about the wearer's waist. Others, however, prefer a trimmer appearance but without the diaper 421 coming unwrapped or folded during wear. Accordingly, in the first configuration of the transverse waist line components 423, the front waist end 427 of the diaper 421 is relatively wider and is substantially decreased in the second configuration of the transverse waist line components 429.

In the illustrated embodiment, lines of weakness 431 are formed in the diaper 421 to extend longitudinally in transversely spaced relationship with each other but spaced transversely inward of the transverse sides of the front waist end 427 of the diaper in the first configuration of the transverse waist line components 423. The lines of weakness 431 may be formed by any of the suitable techniques described previously. To reduce the width of the diaper at the front waist end 427 thereof, the transverse waist line components 423 are separated from the diaper along the respective lines of weakness 431 to decrease the width of the front waist end 427 of the diaper 421 in the second configuration of the transverse waist line components.

It is contemplated that more than one line of weakness 431 may be provided toward each of the transverse sides of the front waist end 427 to provide further selectivity as to the width of the front waist end of the diaper 421. It is also understood that while the transverse waist line components 423 are illustrated in FIGS. 21 and 22 in connection with a diaper, the transverse waist line components may instead be incorporated on pants-type disposable absorbent articles or other absorbent articles without departing from the scope of this invention.

Figure 23:
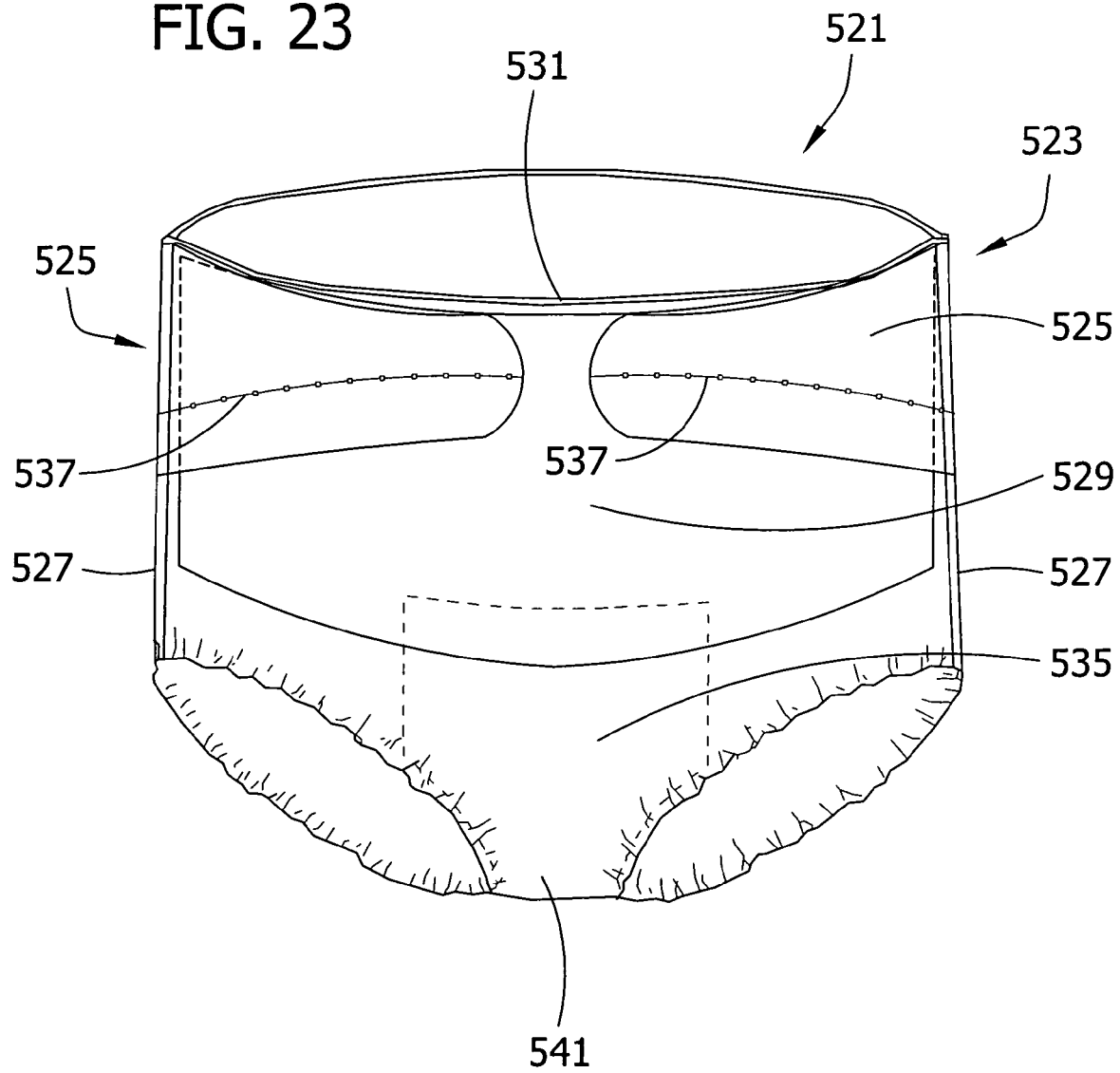
FIG. 23 is a front perspective of a pants-type absorbent article having an elective component in the form of a pair of fastening components, with each fastening component being in a first configuration.
Figure 24:
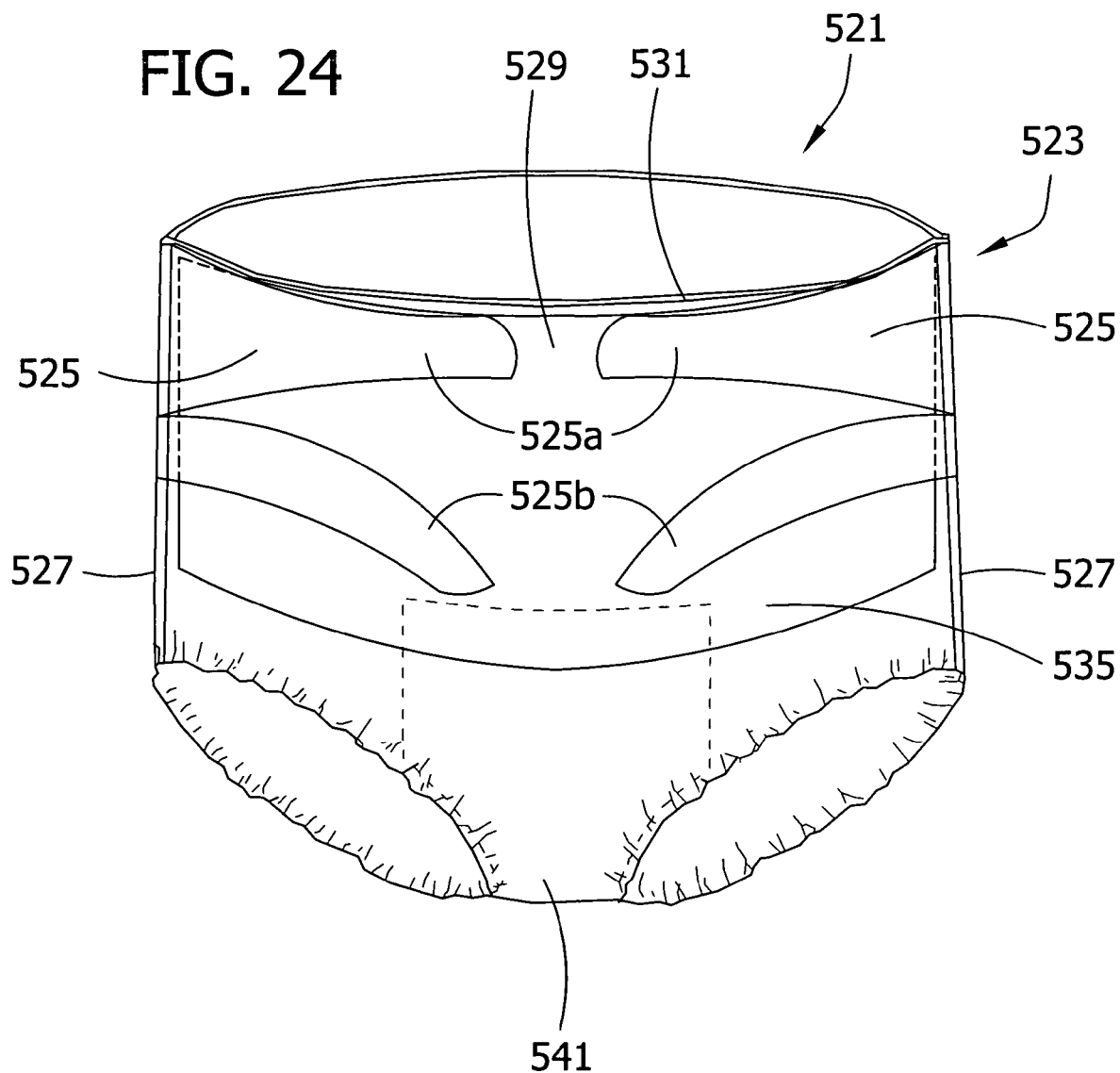
FIG. 24 is a front perspective of the article of FIG. 23 with each fastening component being in a second configuration.

With reference now to FIGS. 23 and 24, a pants-type disposable absorbent article, (broadly, pants) similar to the pants of FIGS. 10-13 is generally indicated at 521. The pants 521 has an elective component in the form of a pair of fastening components 523 each being divisible into a respective pair of fastening tabs 525. As illustrated, a pair of fastening components 523 are secured to the pants 521 generally adjacent side seams 527 at a front region 529 of the pants, and more suitably further adjacent a front waist end 531 of the pants. The fastening components 523 are suitably fastenably engageable with an outer cover 535 of the pants 521. Each of the fastening components 523 has a line of weakness 537 extending longitudinally along at least a portion of thereof, and more suitably substantially the entire length of the fastening component, in the first configuration of the fastening components to define interconnected fastening tabs 525. In this first configuration (FIG. 23), the fastening components 523 are engageable with the outer cover 535 generally adjacent the front waist end 531 of the pants 521.

To improve the fit of the pants 521 on the wearer, the fastening tabs 525 of each fastening component may be separated from each other in a second configuration (FIG. 24) of the fastening components. An upper fastening tab 525A of each fastening component 523 is engaged with the outer cover 535 of the pants 521 generally adjacent the front waist end 531 thereof, while a lower fastening tab 525B is oriented relative to and engaged with the outer cover generally down toward a crotch region 541. The lower fastening tab 525B generally cinches the front leg elastic to provide for a better seal around the leg of the wearer. It is understood that each fastening component 523 may comprise more than two interconnected fastening tabs 525. It is also contemplated that the fastening components 523 may be engageable with corresponding mating fastening components instead of to the outer cover.

Figure 25:
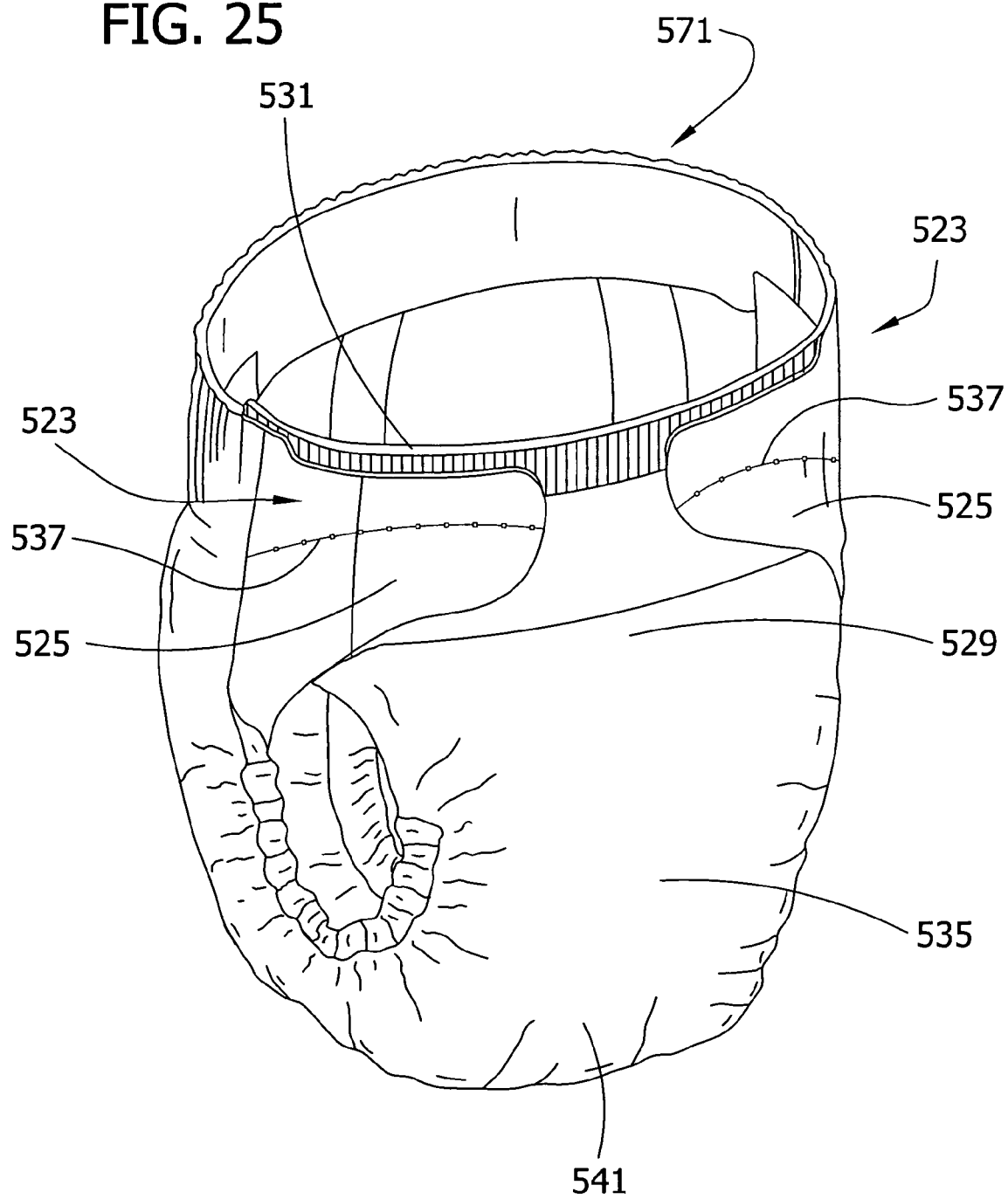
FIG. 25 is a perspective view of a diaper having a fastening component similar to the fastening component of FIG. 23, with the fastening component in a first configuration.
Figure 26:
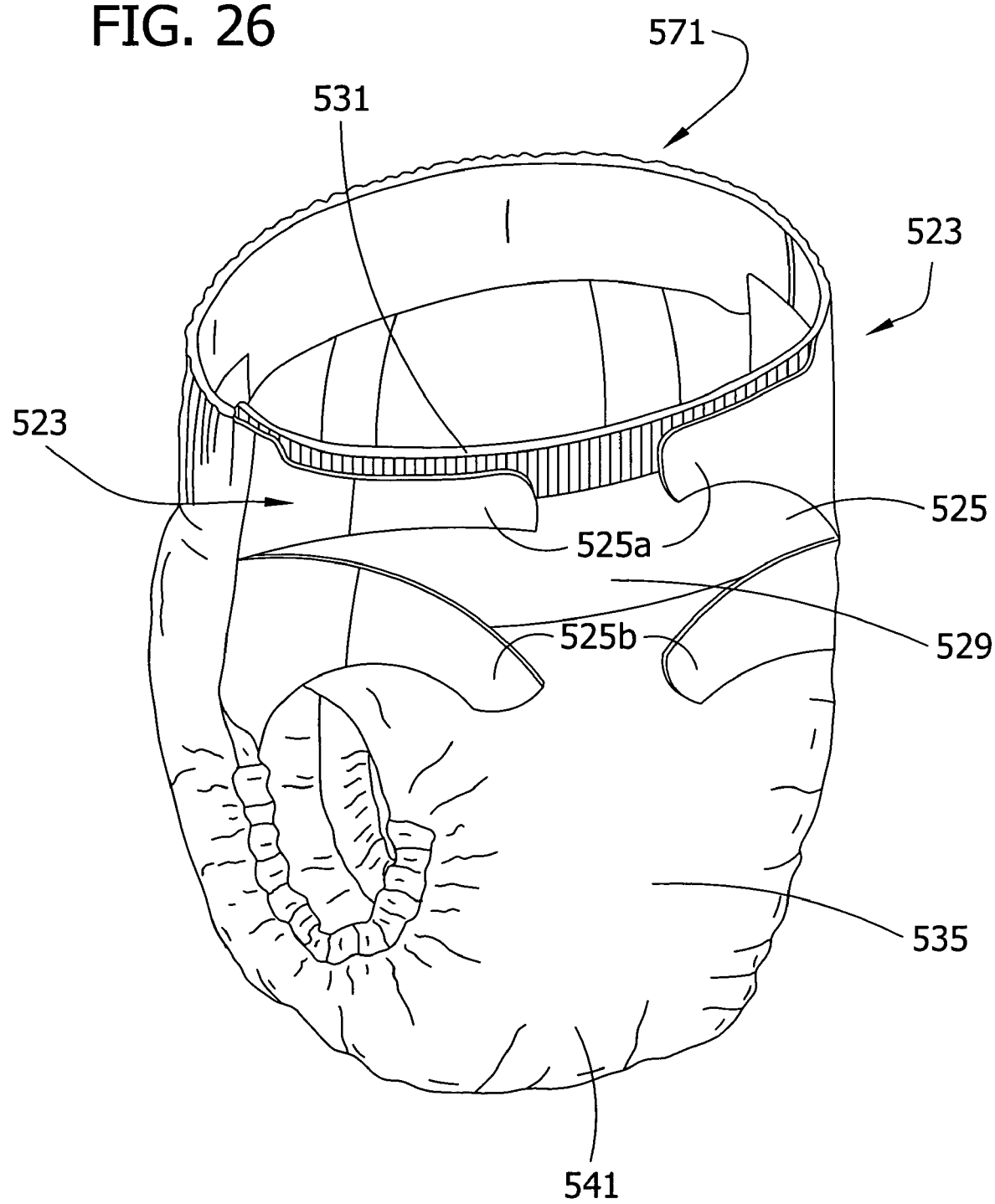
FIG. 26 is a perspective view of the diaper of FIG. 25 with the fastening component in a second configuration.

FIGS. 25-26 illustrate and alternative embodiment in the form of a diaper, generally indicated at 571, in which the divisible fastening components 523 described above replace the fastening tabs 65 of the diaper 21 of FIGS. 1 and 2. The fastening components 523 are illustrated in their first configuration in FIG. 25 on and in their divided, second configuration in FIG. 26.

Figure 27:
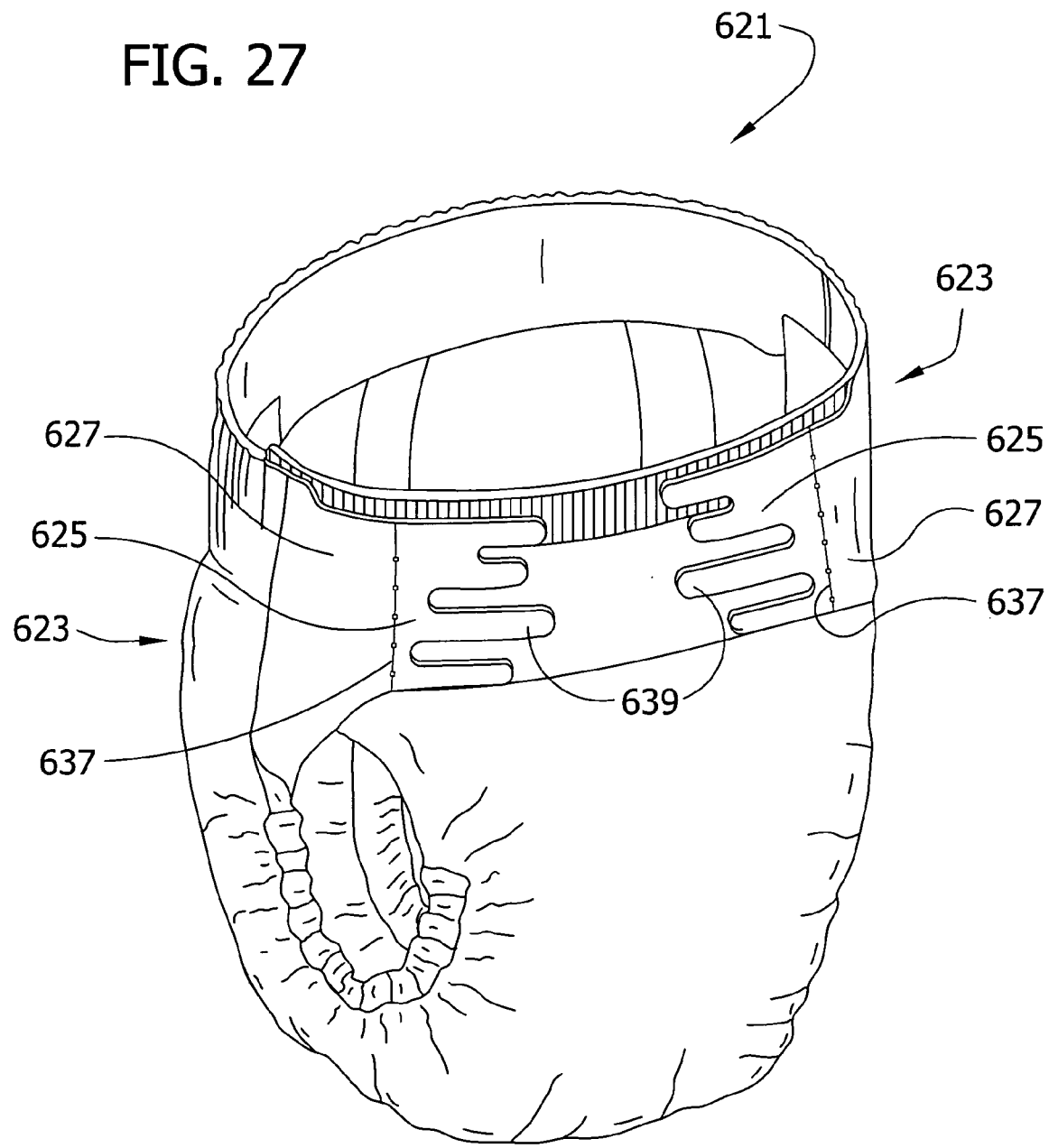
FIG. 27 is a perspective view of a diaper having an elective component in the form of alternative embodiment of a pair of fastening components, with the fastening components being in a first configuration.
Figure 28:
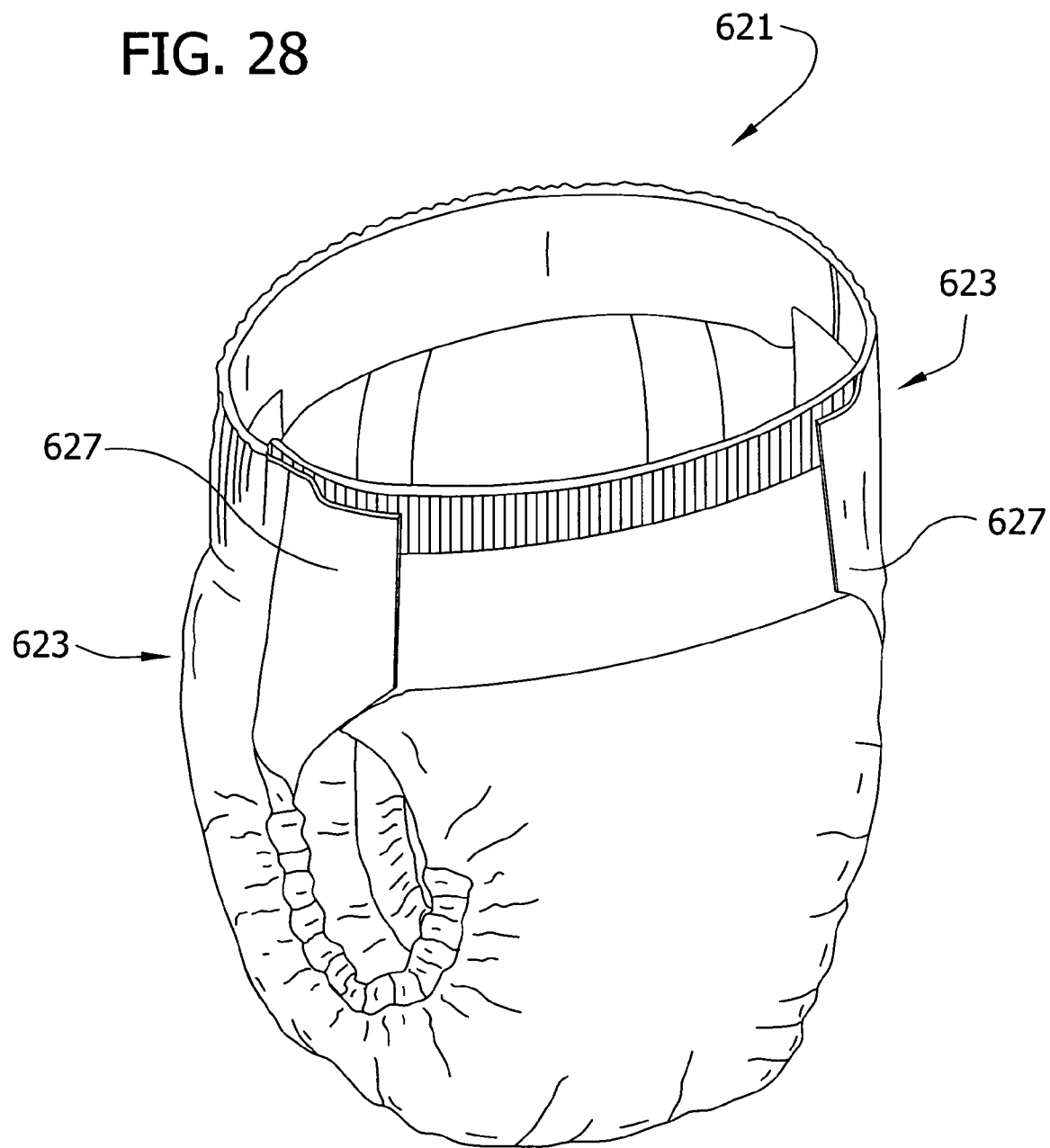
FIG. 28 is a perspective view of the diaper of FIG. 27 with the fastening components in a second configuration.

FIGS. 27-28 illustrate another diaper, generally indicated at 621, having an elective component in the form of fastening components 623 that are selectively adjustable depending on the need to reduce the risk that the child wearing the diaper 621 will unfasten the fastening components. Conventional fastening components typically have generally straight edges that are relatively easy to grasp. As a result, it is not uncommon for young children to unfasten and remove their diapers. In a first configuration of the fastening components 623 of this embodiment, the fastening components are suitably configured to inhibit a young child from unfastening the fastening components (FIG. 27) and is selectively configurable to a second configuration resembling more conventional fastening components in the event there is little risk that the child will unfasten the diaper (FIG. 28).

In the illustrated embodiment, the fastening components 623 each comprise an inner fastener 625 and an outer fastener 627 interconnected to the inner fastener by a line of weakness 637 in the first configuration of the fastening components. The line of weakness 637 is illustrated as a line of perforations in FIG. 27 but may be formed by any of the previously described techniques. The outer fastener 627 is suitably configured to have two or more thin, elongate fingers 639 of fastening material, with the fingers being of variable length. Such a configuration provides an irregular shaped fastener that is difficult for young children to grasp. The fingers 639 are each formed integrally to a common portion of the outer fastener 627, the line of weakness 637 extending through the common portion of the outer fastener.

Where the added protection against the child unfastening the fastening components 623 is not needed, or undesired, the outer fastener 627 is separated from the inner fastener 625 along the line of weakness 637 to configure the fastening component 623 in its second configuration as shown in FIG. 28.

In accordance with one embodiment of a product line of absorbent articles, the product line comprises a first absorbent article (e.g., such as the diaper or pants-type absorbent article described previously) adapted to fit wearers that fall within a first size range, and at least a second absorbent article adapted to fit wearers that fall within a second size range. The term "size range" is used herein to refer to any dimensional difference between one group of wearers and another, such as weight, waist size, or other dimensional difference. For example, in one embodiment, the product line may comprise diapers, with different diapers in the product line being adapted to fit infants in the following weight ranges: less than 6 pounds, less than 10 pounds, 8-14 pounds, 12-18 pounds, 16-28 pounds, 22-37 pounds, greater than 27 pounds, and greater than 35 pounds.

The size ranges for which the product line of absorbent articles are adapted to fit need not be designated by the dimensional characteristic, but rather the size range may instead be designated by other suitable expressions. For example, the size ranges may be expressed in terms of indicative numbers (i.e., 1, 2, 3, etc.), letters (i.e., xs, s, m, l, xl), words (extra small, small, medium, large, extra large), wearer age, or a combination thereof.

The first absorbent article of the product line and the second absorbent article of the product line need not be adapted to fit successive size ranges. Thus, it is contemplated that in some embodiments the size ranges for which the first and second absorbent articles of the product line are adapted to fit overlap each other, while in other embodiments the size ranges for which the first and second absorbent articles of the product line are adapted to fit do not overlap each other. Moreover, the terms "first" and "second" in reference to the first and second absorbent articles of the product line are intended to refer broadly to any two absorbent articles in a product line. Accordingly, the first absorbent article in the product line need as referenced herein need not be the smallest article in the product line (e.g., adapted to the fit the smallest size range). Nor does the second absorbent article need to sequentially follow the first absorbent article with respect to the size ranges for which the articles are adapted to fit. For example, if a product line of absorbent articles comprises five different sized articles (e.g., numbered 1-5 in increasing size), the first and second articles referenced herein may suitably comprise the second and fifth articles of the product line and remain within the scope of this invention.

The first absorbent article of the product line suitably has an elective component that allows selective configuring of the article between the first and second configurations of the elective component. The elective component may be any of the elective components described previously herein and illustrated in the various drawings, or another suitable elective component.

The second absorbent article of the product line suitably has an elective component that is different from the elective component of the first absorbent article. The elective component of the second absorbent article may also be any of the elective components described previously, or another suitable elective component.

As an example, FIGS. 29A and 29B illustrate a product line in which the first and second absorbent articles 721, 821 are diapers similar to the diaper 21 of FIGS. 1 and 2. The first diaper 721 is adapted to fit a wearer size range that corresponds to the age at which a wearer may still have an umbilical cord. The first diaper 721 has an elective component in the form of an umbilical cord component 791 such as the umbilical cord component of FIG. 2 that can be selectively configured from its first configuration to its second configuration to accommodate the wearer's umbilical cord. The second diaper 821 is adapted to fit wearers of a larger size range than that of the first diaper 721 and has an elective component in the form of a waist line component 823 such as the waist line component of FIG. 16 that is selectively configurable from its first configuration to its second configuration to lower the rise of the waist line.

It is contemplated that the second diaper 821 (broadly, the second absorbent article) may have more than one elective component, and one of the elective components on the second diaper may even be the same elective component that is on the first diaper 721, as long as one elective component of the second diaper is different from the elective component of the first diaper.

Figure 30B:
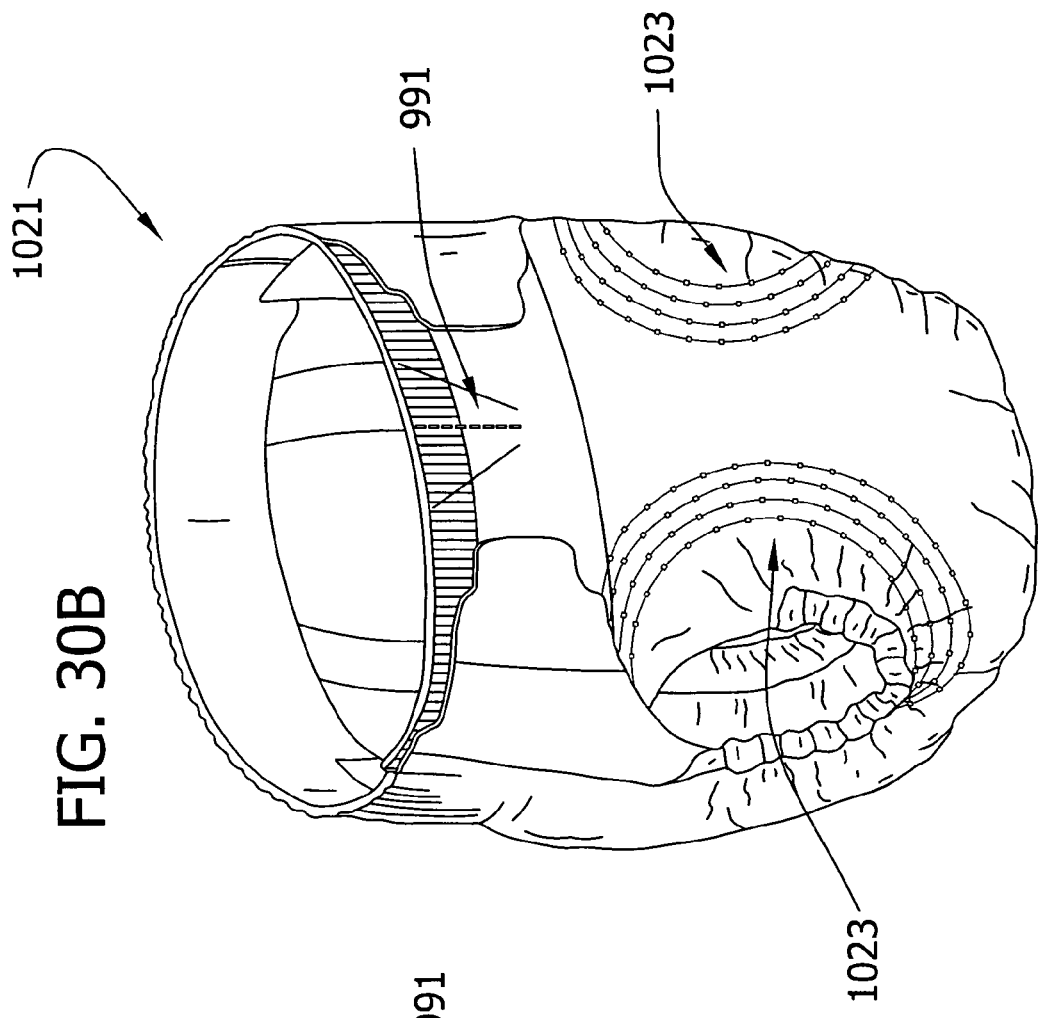
FIG. 30B is a perspective view of a second diaper of the product line, with the second diaper having a first elective component in the form of an umbilical cord component and a second elective component in the form of a leg opening component.
Figure 30A:
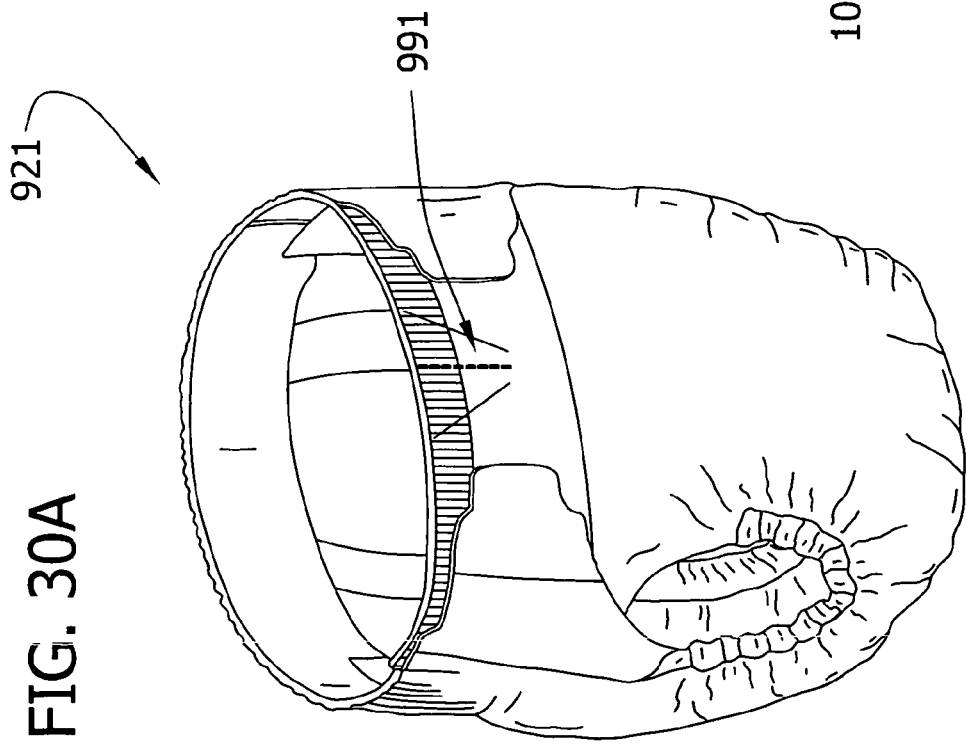
FIG. 30A is a perspective view of a diaper of an alternative embodiment of a product line of absorbent articles, with the diaper having an elective component in the form of an umbilical cord component.

FIGS. 30a, 30b and 30c illustrate another embodiment of a product line of absorbent articles (illustrated as diapers in FIGS. 30a, 30b and 30c) in which a first absorbent article 921 is adapted to fit wearers that fall within a first size range and has an elective component—in the illustrated embodiment, an umbilical cord component 991 similar to the umbilical cord component 91 of FIG. 2.

The second absorbent article 1021 (FIG. 30b) is adapted to fit wearers that fall within a second size range that is at least in part different from (e.g., greater than) the first size range for which the first absorbent article is adapted to fit. The second absorbent article 1021 has the same elective component (e.g., umbilical cord component 991) as the first absorbent article 921, and also has another elective component—in the illustrated embodiment, leg opening components 1023 similar to the leg opening components of FIG. 10—different from the elective component of the first absorbent article.

The third absorbent article 1121 (FIG. 30c) is adapted to fit wearers that fall within a third size range that is at least in part different from both the first and second sizes for which the first and second absorbent articles 921, 1021 are adapted to fit. The third absorbent article 1121 has at least one elective component (e.g., leg opening components 1023) that is the same as one of the elective components of the second absorbent article 1021, and at least one other elective component that is different from both of the elective components of the second absorbent article—in the illustrated embodiment, a waist line component 1123 similar to the waist line component of FIG. 16.

It is contemplated that the first absorbent article 921 of the product line may have more than one elective component, as long as the first and second absorbent articles share a common elective component. It is understood that the absorbent articles of the product line may be other than diapers, such as the pants-type absorbent articles described previously and illustrated in the drawings. It is also understood that the elective components of the product line absorbent articles may be other than those illustrated in FIGS. 30a, 30b and 30c, such as any of the elective components described previously or other suitable elective components, without departing from the scope of this invention.

In another embodiment, a product line of absorbent articles may comprise a first absorbent article having an elective component that is selectively configurable to accommodate a particular body characteristic of the wearer. The term body characteristic refers to a particular physical body feature such as waist size, thigh size, umbilical cord, or other physical body feature. A second absorbent article of the product line has an elective component different from the elective component of the first absorbent article and is selectively configurable to accommodate a body characteristic different from the body characteristic for which the first absorbent article is adapted to accommodate. The second absorbent article may be adapted to fit wearers within the same size range as the first absorbent article, or a size range different from the size range for which the first absorbent article is adapted to fit.

Figure 31B:
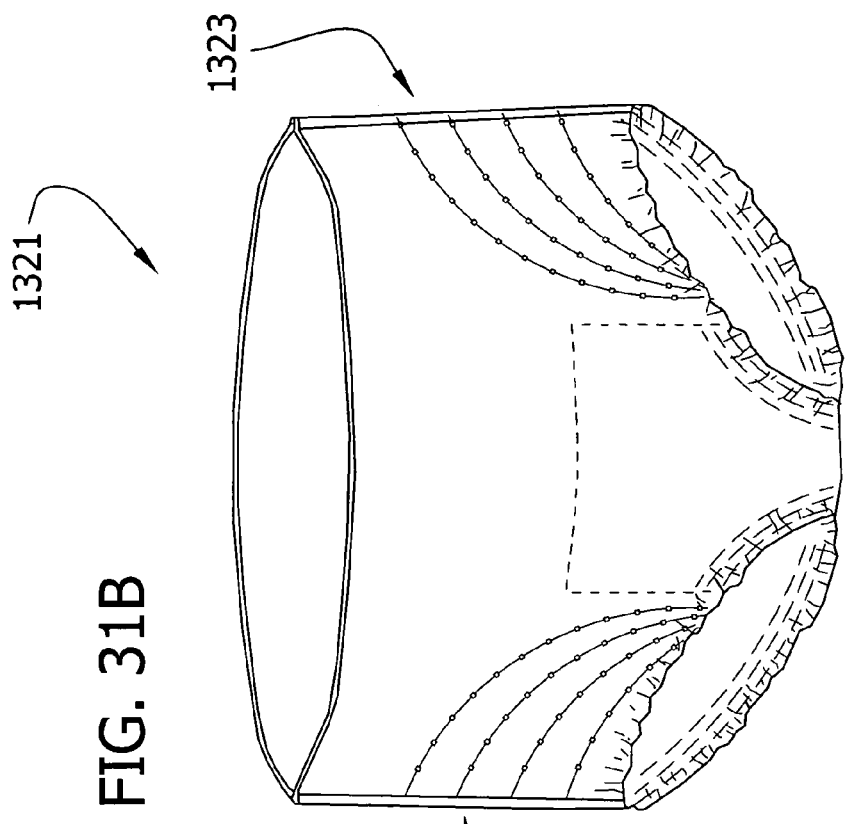
FIG. 31B is a front perspective of a second pants-type article of the product line, with the second article having an elective component in the form of a leg opening component.
Figure 31A:
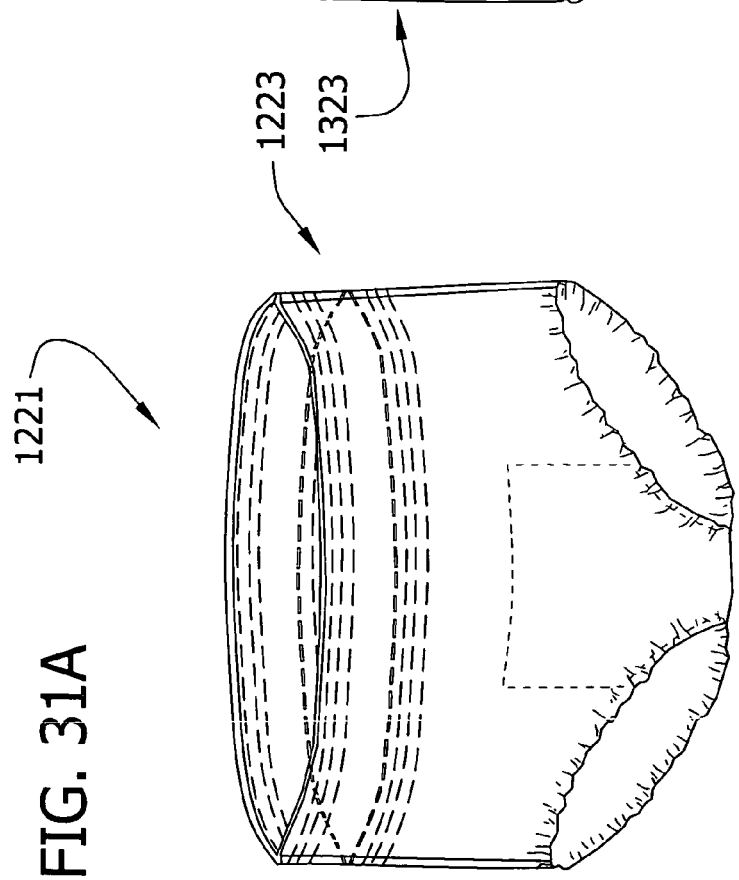
FIG. 31A is a front perspective of a first pants-type article of a third embodiment of a product line of absorbent articles, with the first article having an elective component in the form of a waist line component.

The elective components of the first and second absorbent articles may be any of the elective components described previously and illustrated in the various drawings herein, or other suitable elective components. For example, in the illustrated embodiment of FIGS. 31a and 31b, the first and second absorbent articles 1221, 1321 are pants-type absorbent articles such as that described previously and illustrated in FIGS. 10-13. The first absorbent article 1221 comprises an elective component in the form of a waist line component 1223 that is selectively configurable to accommodate the wearer's waist line, and in particular to reduce the rise of the pants waist line. The second absorbent article 1321 has an elective component in the form of leg opening components 1323 that are selectively configurable to accommodate the wearer's thighs, and in particular to increase the circumference of the leg openings of the pants.

In another embodiment the first absorbent article may have a permanent feature (i.e., non-elective) designed to accommodate a particular body characteristic, and the second absorbent article may have an elective component that is selectively configurable to accommodate the same body characteristic. For example, in the embodiment of FIGS. 32a and 32b, a first absorbent article 1421 (FIG. 32a) is in the form of a diaper similar to the diaper of FIGS. 1 and 2, but with a front waist end 1423 of the diaper configured (e.g., having a cut-out 1425) to accommodate an umbilical cord of the wearer. A second absorbent article 1521 (FIG. 32b) is also in the form of a diaper but instead has an elective component in the form of an umbilical cord component 1591 similar to the umbilical cord component 91 of FIG. 2. The umbilical cord component 1591 is selectively configurable from a first configuration to a second configuration to accommodate an umbilical cord of the wearer.

It is understood that the first and/or second absorbent articles 1421, 1521 of the product line of this embodiment may be other than a diaper. The permanent feature of the first absorbent article 1421 and the elective component of the second absorbent article 1521 may also be other than those illustrated in FIGS. 32a and 32b without departing from the scope of this invention. It is also contemplated that the first absorbent article 1421 may also have one or more elective components, and/or the second absorbent article 1521 may have more than one elective component and remain within the scope of this invention.

Figure 33B:
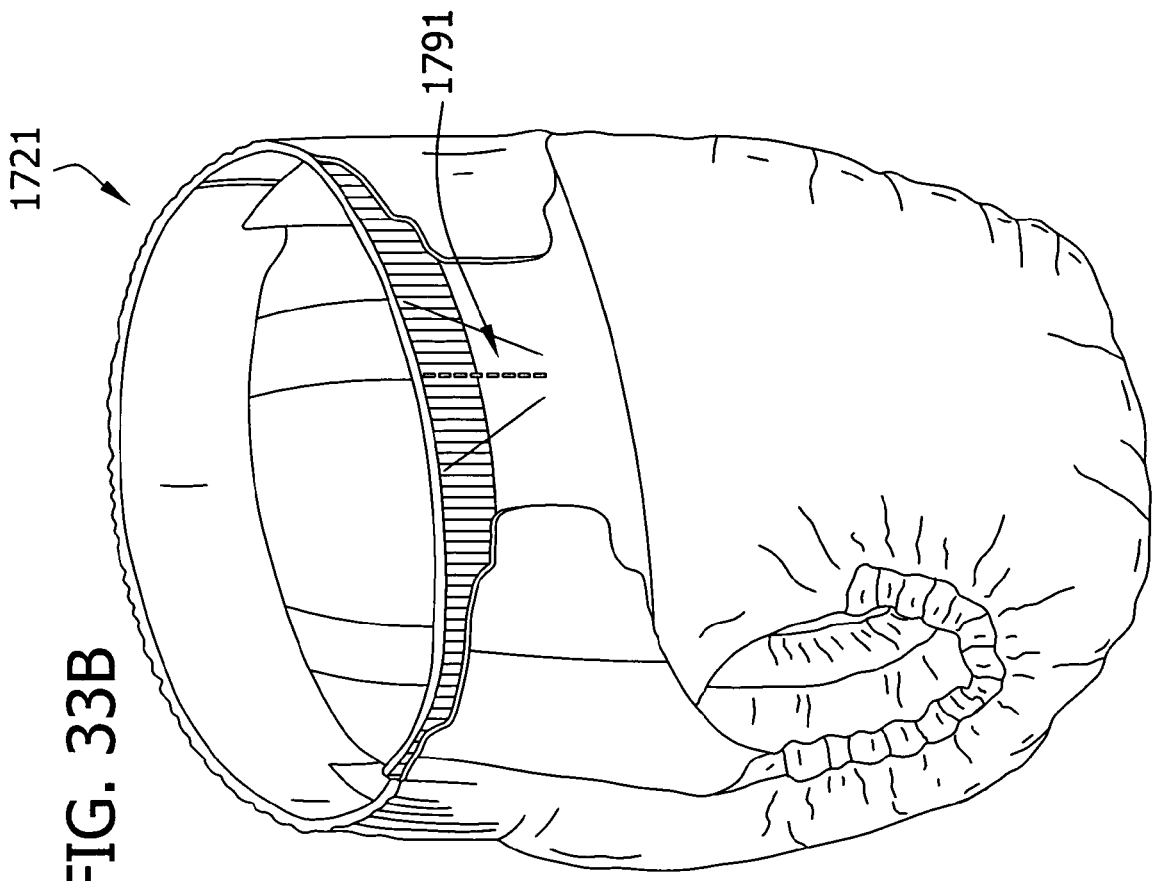
FIG. 33B is a perspective view of a second diaper of the product line with the diaper being of a different size that the first diaper and having an elective component in the form of an umbilical cord component.
Figure 33A:
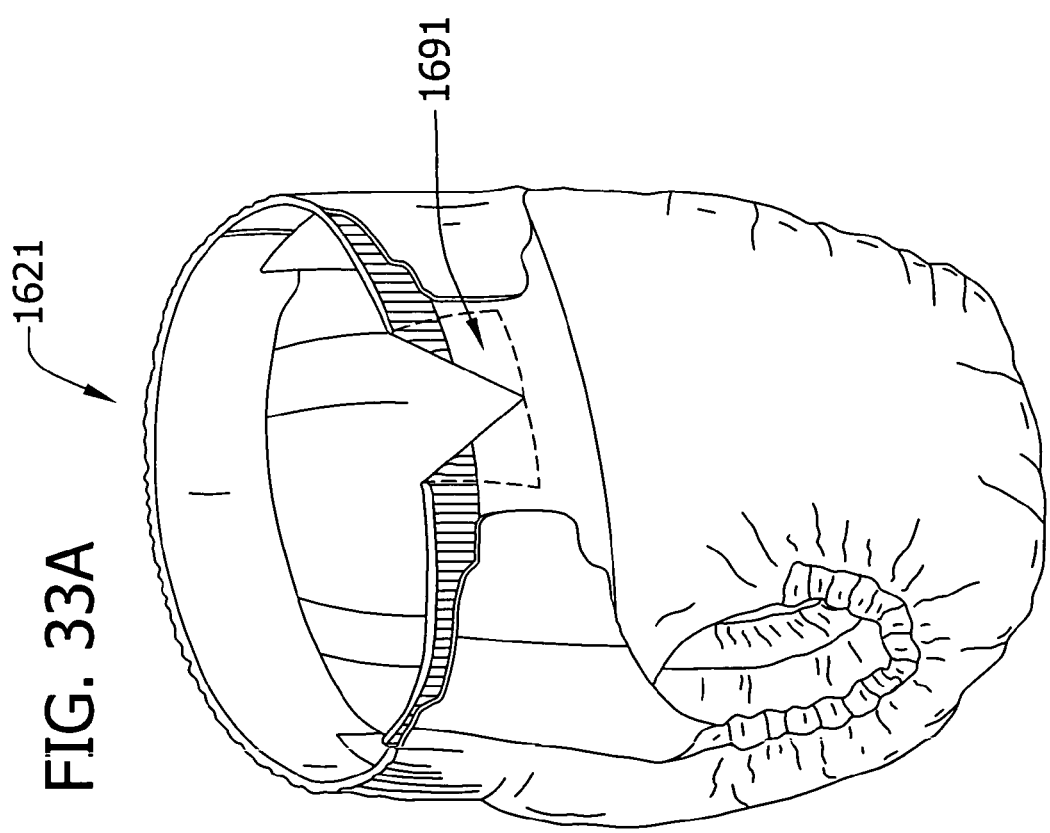
FIG. 33A is a perspective view of a first diaper of a fifth embodiment of a product line of absorbent articles with the first diaper having an elective component in the form of an umbilical cord component, the component being show in a second configuration thereof to accommodate an umbilical cord of the wearer.

FIGS. 33a and 33b illustrate an embodiment of a product line of absorbent articles having a first absorbent article 1621 in the form of a diaper adapted to fit wearers falling with a first size range, and a second absorbent article 1721 also in the form of a diaper and adapted to fit wearers of a second range that is at least in part different from the size range for which the first absorbent article is adapted to fit. For example, in the illustrated embodiment the second diaper 1721 is sized larger than the first diaper 1621 but is adapted to fit wearers that fall within a size range that overlaps the upper end of the size range for which the first diaper is adapted to fit but is otherwise greater than the size range for which the first diaper is adapted to fit. It is understood, however, that the size range for which the second diaper 1721 is adapted to fit may not overlap any portion of the size range for which the first diaper 1621 is adapted to fit.

As illustrated in FIG. 33a, the first diaper 1621 has an elective component (in the illustrated embodiment, an umbilical cord component 1691) that is selectively configurable from a first configuration to a second configuration (e.g., wherein the umbilical cord component is configured to accommodate the wearer's umbilical cord). In particular, the first diaper 1621 is suitably sized such that the elective component of the first diaper is intended to be used in its second configuration for a majority of wearer's that fall within the first size range and in its first configuration for a minority of wearer's that fall within the first size range. For example, the first diaper 1621 is suitably sized for use by newborns that fall within a size range that encompasses a majority of all newborns. Accordingly, most of the newborns that fall within this size range will need the umbilical cord component 1691 in its second (e.g., removed/folded) configuration to accommodate the umbilical cord).

The second diaper 1721 also has an elective component in the form of an umbilical cord component 1791 that is selectively configurable from a first configuration to a second configuration (e.g., wherein the umbilical cord component is configured to accommodate the wearer's umbilical cord). In particular, the second diaper 1721 is suitably sized such that the elective component of the second diaper is intended to be used in its second configuration for a minority of wearer's that fall within the second size range and in its first configuration for a majority of wearer's that fall within the first size range. For example, the second diaper 1721 is suitably sized for use by newborns or slightly larger infants that fall within a size range that encompasses a smaller minority of all newborns. Accordingly, only a minority number of wearer's of the second diaper 1721 will still have an umbilical cord and require the diaper to be configured with the umbilical cord component 1791 in its second configuration. The majority of wearer's of the second diaper 1721 will instead have the diaper configured with the umbilical cord component 1791 in its first configuration as illustrated in FIG. 33b.

It is understood that the first and/or second absorbent articles 1621, 1721 of the product line of this embodiment may be other than a diaper. The common elective component of the first and second absorbent articles 1621, 1721 may be other than the umbilical cord components 1691, 1791 illustrated in FIGS. 33a and 33b. It is also contemplated that the first absorbent article 1621 may have more than one elective component, and/or the second absorbent article 1721 may have more than one elective component and remain within the scope of this invention.

When introducing elements of the present invention or the preferred aspect(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or illustrated in the accompanying drawings shall be interpreted as illustrative and not in a limiting sense.

What is claimed is:

1. A product line of absorbent articles, said product line comprising a first absorbent article adapted to fit wearers sized within a first size range, said first absorbent article comprising an outer cover, a liquid permeable bodyside liner in opposed relationship with the outer cover, an absorbent body disposed between the liner and the outer cover for absorbing liquid that passes through the liner, and a first elective component secured to the first absorbent article in a first configuration of said component and selectively configurable to a second configuration different from the first configuration of said component; and a second absorbent article adapted to fit wearers sized within a second size range at least in part different from said first size range, said second absorbent article comprising an outer cover, a liquid permeable bodyside liner in opposed relationship with the outer cover, an absorbent body disposed between the liner and the outer cover for absorbing liquid that passes through the liner, a first elective component substantially the same as the first elective component of the first absorbent article and a second elective component different from said first elective component and secured to the second absorbent article in a first configuration of said second elective component, said second elective component being selectively configurable to a second configuration different from the first configuration of said second elective component; and a third absorbent article adapted to fit wearers sized within a third size range at least in part different from said first size range and at least in part different from said second size range, said third absorbent article comprising an outer cover, a liquid permeable bodyside liner in opposed relationship with the outer cover, an absorbent body disposed between the liner and the outer cover for absorbing liquid that passes through the liner, a first elective component substantially the same as at least one of the first elective component of the second absorbent article and the second elective component of the second absorbent article, and a second elective component different from said first elective component of said third absorbent article and secured to the third absorbent article in a first configuration of said second elective component, said second elective component being selectively configurable to a second configuration different from the first configuration of said second elective component.

2. The product line set forth in claim 1 wherein at least one of the elective components of one of said first, second and third absorbent articles comprises an umbilical cord component secured to said absorbent article in a first configuration of the umbilical cord component and selectively configurable to a second configuration in which the umbilical cord component is at least in part detached from said absorbent article to accommodate an umbilical cord of the wearer.

3. The product line set forth in claim 2 wherein the umbilical cord component remains in part attached to said absorbent article in the second configuration of said component.

4. The product line set forth in claim 2 wherein in the first configuration of the umbilical cord component said component is attached to said absorbent article along at least one line of weakness, in the second configuration of the umbilical cord component said component being detached from said absorbent article along said at least one line of weakness.

5. The product line set forth in claim 1 wherein said first, second and third absorbent articles are configured for wearing about a wearer's waist and each comprises a waist line defining a central waist opening, said absorbent articles each further having a pair of leg openings, at least one of the elective components of one of said first, second and third absorbent articles comprises at least one waist line component attached to the absorbent articles in the first configuration of said waist line components and selectively configurable to a second configuration of said waist line components in which the waist line of the absorbent article is disposed at a lower position on the wearer's waist than in the first configuration of the waist line component.

6. The product line set forth in claim 1 wherein the first, second, and third absorbent articles are configured for wearing about a wearer's waist and each comprises a waist line defining a central waist opening, each of said absorbent articles further having a pair of leg openings, at least one of the elective components of one of said first, second, and third elective components comprise first and second leg opening components attached to the respective first and second absorbent articles in the first configuration of said leg opening components and selectively configurable to the second configuration of said leg opening components in which the leg openings of the respective absorbent article each have a second circumference greater than said first circumference.

7. The product line set forth in claim 1 wherein the first, second, and third absorbent articles are configured for wearing about a wearer's waist, each having a longitudinal direction generally from a front end to a back end of the article and a transverse direction extending widthwise of the article, at least one of the elective components of one of said first, second, and third elective components comprising a transverse waist line component selectively configurable from a first configuration of the waist line component to a second configuration different from the first configuration, the article having a first width at one of the front end and the back end in the first configuration of the transverse waist line component and a second width at said one of the front end and the back end of the article in the second configuration of the transverse waist line component, said second width being substantially less than said first width.

8. The product line set forth in claim 1 wherein the first, second, and third absorbent articles are configured for wearing about a wearer's waist and each comprises a waist line defining a central waist opening, at least one of the elective components of one of said first, second, and third elective components comprising a fastening component for use in securing the article on the wearer's waist, in a first configuration of the fastening component, said component comprising a single fastening member engageable with at least one of another fastening member and the outer cover generally at the waist thereof, the fastening component being configurable to a second configuration in which the fastening component is configured as a pair of fastening components, one of which is engageable with said at least one of another fastening component and the outer cover generally at the waist thereof.

9. The product line set forth in claim 1 wherein the first, second, and third absorbent articles are configured for wearing about a wearer's waist and each comprises a waist line defining a central waist opening, at least one of the elective components of one of said first, second, and third elective components comprising a fastening component for use in securing the article on the wearer's waist, said component comprising a fastening member engageable with at least one of another fastening member and the outer cover generally at the waist thereof, in a first configuration of the fastening component at least one of the fastening members having fingers for making the fastening member more difficult to grip, the fastening component being configurable to a second configuration in which the fastening component is substantially free of fingers.

* * * * *

UNITED STATES PATENT AND TRADEMARK OFFICE
CERTIFICATE OF CORRECTION

PATENT NO. : 7,641,641 B2 Page 1 of 1
APPLICATION NO. : 11/110512
DATED : January 5, 2010
INVENTOR(S) : Dana L. Ramshak It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 766 days.

Signed and Sealed this

Twenty-first Day of December, 2010

David J. Kappos
*Director of the United States Patent and Trademark Office*